US009376461B2

(12) United States Patent
Koppetsch et al.

(10) Patent No.: US 9,376,461 B2
(45) Date of Patent: Jun. 28, 2016

(54) NON-ENZYMATIC SYNTHESIS OF O-ACETYL-ADP-RIBOSE AND ANALOGUES THEREOF

(75) Inventors: Karsten Koppetsch, Cambridge, MA (US); Bruce G. Szczepankiewicz, Cambridge, MA (US); Robert B Perni, Cambridge, MA (US)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 64 days.

(21) Appl. No.: 14/124,395

(22) PCT Filed: Jun. 6, 2012

(86) PCT No.: PCT/US2012/041053
§ 371 (c)(1),
(2), (4) Date: Dec. 6, 2013

(87) PCT Pub. No.: WO2012/170494
PCT Pub. Date: Dec. 13, 2012

(65) Prior Publication Data
US 2015/0218202 A1  Aug. 6, 2015

Related U.S. Application Data

(60) Provisional application No. 61/493,677, filed on Jun. 6, 2011.

(51) Int. Cl.
*C07H 19/20* (2006.01)
*C07H 19/207* (2006.01)
*C07H 1/00* (2006.01)
*C07H 13/04* (2006.01)

(52) U.S. Cl.
CPC .............. *C07H 19/20* (2013.01); *C07H 1/00* (2013.01); *C07H 13/04* (2013.01)

(58) Field of Classification Search
CPC ........... C07H 1/00; C07H 19/20; C07H 13/04
See application file for complete search history.

(56) References Cited

U.S. PATENT DOCUMENTS

| | | | |
|---|---|---|---|
| 6,987,091 | B2 | 1/2006 | Schramm et al. |
| 7,291,606 | B2 | 11/2007 | Denu et al. |
| 7,432,246 | B2 | 10/2008 | Schramm et al. |
| 7,521,432 | B2 | 4/2009 | Denu et al. |
| 7,670,806 | B2 * | 3/2010 | Moss et al. ................. 435/72 |
| 7,741,295 | B2 | 6/2010 | Schramm et al. |
| 2010/0036142 | A1 | 2/2010 | Rongione et al. |

FOREIGN PATENT DOCUMENTS

WO  WO 02/38579 A1   5/2002
WO  WO 03/045907 A2  6/2003

OTHER PUBLICATIONS

Romero, et al., "Secondary Deuterium Isotope Effects for Acid-Catalyzed Hydrolysis of Inosine and Adenosine", *Journal of the American Chemical Society*, vol. 100, pp. 7620-7624 (1978).
PCT International Search Report and Written Opinion, 10 pages, PCT/US12/41053, Aug. 28, 2012.
Szczepankiewicz, et al., "One-Step, Nonenzymatic Synthesis of O-Acetyl-ADP-ribose and Analogues from NAD and Carboxylates", *J. Org. Chem.*, vol. 76, pp. 6465-6474 (2011).
Liu, et al., "Identification and Characterization of Propionylation at Histone H3 Lysine 23 in Mammalian Cells", *The Journal of Biological Chemistry*, vol. 284, No. 47, pp. 32288-32295 (2009).
Sauve, A. A., "Sirtuin chemical mechanisms", *Biochimica et Biophysica Acta*, vol. 1804, pp. 1591-1603 (2010).
Sauve, et al., "Chemistry of Gene Silencing: The Mechanism of NAD+-Dependent Deacetylation Reactions", *Biochemistry*, vol. 40, pp. 15456-15463 (2001).
Gazzaniga, et al., "Microbial NAD Metabolism: Lessons from Comparative Genomics", *Microbiology and Molecular Biology Reviews*, vol. 73, No. 3, pp. 529-541 (2009).
Denu, John M., "The Sir2 family of protein deacetylases", *Current Opinion in Chemical Biology*, vol. 9, pp. 431-440 (2005).
Sauve, et al., "SIR2: The Biochemical Mechanism of NAD+-Dependent Protein Deacetylation and ADP-Ribosyl Enzyme Intermediates", *Current Medicinal Chemistry*, vol. 11, pp. 807-826 (2004).
Tanner, et al., "Silent information regulator 2 family of NAD-dependent histone/protein deacetylases generates a unique product, 1-O-acetyl-ADP-ribose", *PNAS*, vol. 97, No., pp. 14178-14182 (2000).
Tong, et al., "Function and metabolism of sirtuin metabolite O-acetyl-ADP-ribose", *Biochimica et Biophysica Acta*, vol. 1804, pp. 1617-1625 (2010).
Lee, et al., "Quantification of Endogenous Sirtuin Metabolite Oacetyl-ADP-Ribose (OAADPR)", *Anal. Biochem.*, vol. 383, No. 2, pp. 174-179 (2008).
Hoff, et al., "Getting a grip on O-acetyl-ADP-ribose" *Nat. Struct. Mol. Biol.*, vol. 12, No. 7, pp. 560-561 (2005).
Borra, et al., "Conserved Enzymatic Production and Biological Effect of O-Acetyl-ADP-ribose by Silent Information Regulator 2-like NAD+-dependent Deacetylases", *The Journal of Biological Chemistry*, vol. 277, No. 15, pp. 12632-12641 (2002).
Norris, et al., "Silent information regulator 3: the Goldilocks of the silencing complex", *Genes Dev.*, vol. 24, pp. 115-122 (2010).
Ono, et al., "The 39-kDa poly (ADP-ribose) glycohydrolase ARH3 hydrolyzes O-acetyl-ADP-ribose, a product of the Sir2 family of acetyl-histone deacetylases", *PNAS*, vol. 103, No. 45, pp. 16687-16691 (2006).

(Continued)

*Primary Examiner* — Lawrence E Crane
(74) *Attorney, Agent, or Firm* — Kathryn A. Lutomski; Edward R. Gimmi; William R. Majarian

(57) ABSTRACT

Provided herein is a simple, one-step, non-enzymatic synthesis of O-Acetyl-ADP-ribose (OAADPR) from NAD and sodium acetate in acetic acid. The extension of this reaction to other carboxylic acids, demonstrates that the reaction between NAD, and NAD analogs produces mixtures of the corresponding 2'- and 3'-carboxylic esters. Included are O-carboxyl-ADP-ribose compounds and corresponding methods of synthesis (e.g., O-propionyl-ADP-ribose, O-succinyl-ADP-ribose, O-malonyl-ADP-ribose), as well as non-adenosine nucleoside compounds.

42 Claims, 10 Drawing Sheets

(56) References Cited

OTHER PUBLICATIONS

Chen, et al., "Identification of Macrodomain Proteins as Novel O-Acetyl-ADP-ribose Deacetylases", *The Journal of Biological Chemistry*, vol. 286, No. 15, pp. 13261-13271 (2011).

Comstock, et al., "Synthesis and biochemical evaluation of O-acetyl-ADP-ribose and N-acetyl analogs", *Org. Biomol. Chem.*, vol. 5, pp. 3087-3091(2007).

Jackson, et al., "Structural Identification of 2'- and 3'-O-Acetyl-ADP-ribose as Novel Metabolites Derived from the Sir2 Family of β-NAD+-dependent Histone/Protein Deacetylases", *The Journal of Biological Chemistry*, vol. 277, No. 21, pp. 18535-18544 (2002).

Bazin, et al., "Reinvestigation of 4-Thiothymidine-5'-Triphosphate Synthesis", *Nucleosides & Nucleotides*, vol. 18, Nos. 4&5, pp. 965-966 (1999).

Hirota, et al., "Pyrimidine Derivatives and Related Compounds. XLIX.[1)] Reaction of Anhydrouridines with the Vilsmeier Reagent". *Chem. Pharm. Bull.* vol. 32, No. 7, pp. 2591-2595 (1984).

Hunston, et al., "Synthesis of 2'-deoxy-5-fluoro-5'-O-1",3",2"-oxazaphosphacyclohexa-2"-yluridine 2"-oxide and related compounds", *Tetrahedron*, vol. 36, pp. 2337-2340 (1980).

Tono-Oka, et al., "Terminal Diols as Efficient Substrates for Transglycosylational Activity of NAD Glycohydrolase", *Nucleosides & Nucleotides*, vol. 18, pp. 39-49 (1999).

Kasamatsu, et al., "Hydrolysis of O-Acetyl-ADP-ribose Isomers by ADP-ribosylhydrolase 3", *The Journal of Biological Chemistry*, vol. 286, pp. 21110-21117, (2011).

Tarnus, et al., "Chemical Evidence in Favor of a Stabilized Oxocarbonium-Ion Intermediate in the NAD+ Glycohydrolase-Catalyzed Reactions", *Bioorganic Chemistry*, vol. 16, pp. 38-51 (1988).

Bull, et al., "Concerning the Mechanism of the Enzymatic and Nonenzymatic Hydrolysis of Nicotinamide Nucleotide Coenzymes", *The Journal of Biological Chemistry*, vol. 253, No. 14, pp. 5836-5192 (1978).

Dudev, et al., "Factors Controlling the Mechanism of NAD+ Non-Redox Reactions", *J. Am. Chem. Soc.*, vol. 132, pp. 16533-16543 (2010).

Cervantes-Laurean, et al., "Preparation of low molecular weight model conjugates for ADP-ribose linkages to protein", *Methods in Enzymology*, vol. 280, pp. 275-287 (1997).

Garrity, et al., "N-Lysine Propionylation Controls the Activity of Propionyl-CoA Synthetase", *The Journal of Biological Chemistry*, vol. 282, No. 41, pp. 30239-30245 (2007).

Smith, et al., "Acetyl-lysine Analog Peptides as Mechanistic Probes of Protein Deacetylases", *The Journal of Biological Chemistry*, vol. 282, No. 51, pp. 37256-37265 (2007).

Hassa, et al., Nuclear ADP-Ribosylation Reactions in Mammalian Cells: Where Are We Today and Where Are We Going?, Microbiology and Molecular Biology Reviews, vol. 70, No. 3789-829 (2006).

* cited by examiner

2a: R₁ = H, R₂ = Ac
2b: R₁ = Ac, R₂ = H

Guanosine 5-methyluridine

Uridine

Cytidine

Mesylate

Triflate

Tosylate

Benzenesulfonate

Propionic Acid n-Butyric Acid

Isobutyric Acid

Trimethylacetic Acid trans-Butenoic Acid n-Pentanoic acid 3,3-Dimethylacrylic Acid n-Hexanoic Acid n-Heptanoic Acid Benzoic acid Succinic Acid Citric Acid DL-Lactic Acid L-Malic Acid

| number | shift (ppm) | multiplicity | integration | coupling constant (Hz) | assignment[a] |
|---|---|---|---|---|---|
| 1 | 8.58 | s | 1 | | H2''' (purine) |
| 2 | 8.32 | s | 1 | | H8''' (purine) |
| 3 | 6.07 | d | 1 | 5.4 | H1'' |
| 4 | 5.41 | d | 0.34 | 4.2 | H1'β |
| 5 | 5.18 | d | 0.66 | 1.7 | H1'α |
| 6 | 4.91 | dd | 0.34 | 5.8, 4.2 | H2'β |
| 7 | 4.85 | dd | 0.66 | 5.1, 1.7 | H2'α |
| 8 | 4.65 | m | 1 | | H2'' |
| 9 | 4.44 | m | 1 | | H3'' |
| 10 | 4.38 | dd | 0.66 | 6.2, 5.2 | H3'α |
| 11 | 4.28 | m | 1.34 | | H4'', H3'β |
| 12 | 4.23-3.90 | m | 5 | | H4'', H5'', H4'α, H4'β, H5'α, H5'β |
| 13 | 2.32 | m | 2 | | H2 (Bu) |
| 14 | 1.51 | m | 2 | | H3 (Bu) |
| 15 | 0.80 | t | 0.9 | 7.4 | H4 (Bu) |
| 16 | 0.79 | t | 2.1 | 7.4 | H4 (Bu) | a) α or β refer to the 1'-OH stereochemistry, and not to the individual proton stereochemistries.

| number | shift (ppm) | multiplicity | integration | coupling constant (Hz) | assignment[a] |
|---|---|---|---|---|---|
| 1 | 8.56 | s | 1 | | H2''' (purine) |
| 2 | 8.33 | s | 1 | | H8''' (purine) |
| 3 | 6.08 | d | 1 | 5.4 | H1'' |
| 4 | 5.3 | d | 0.5 | 4.6 | H1'β |
| 5 | 5.1 | d | 0.5 | 3.6 | H1'α |
| 6 | 5.02 | m | 1 | | H3'β, H3'α |
| 7 | 4.66 | m | 1 | | H2'' |
| 8 | 4.44 | t | 1 | 4.4 | H3'' |
| 9 | 4.3 | m | 1 | | H4'' |
| 10 | 4.23 | m | 1 | | H4'β, H2'β |
| 11 | 4.13 | m | 3 | | H5'', H4'α, H4'β |
| 12 | 4.11 | m | 2 | | H5' |
| 13 | 2.28 | t | 2 | 7.3 | H2 (Bu) |
| 14 | 1.47 | m | 2 | | H3 (Bu) |
| 15 | 0.78 | t | 1.5 | 7.4 | H4 (Bu) |
| 16 | 0.78 | t | 1.5 | 7.4 | H4 (Bu) | a) α or β refer to the 1'-OH stereochemistry, and not to the individual proton stereochemistries.

Figure 10

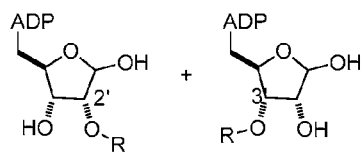

| Entry | Cmpd. | R = | Conditions[a] | Yield (%)[b] |
|---|---|---|---|---|
| 1 | 2 | Acetate | A | 36 [c] (62)[d] |
| 2 | 3 | Propionate | A | 12[e] |
| 3 | 4 | n-Butyrate | A | 12[e] |
| 4 | 5 | Isobutyrate | A | 5[e] |
| 5 | 6 | Trimethylacetate | A | 1[e] |
| 6 | 7 | trans-2-Butenoate | A | 17[e] |
| 7 | 8 | n-Pentanoate | A | 18[e] |
| 8 | 9 | 3,3-Dimethylacrylate | A | 13[e] |
| 9 | 10 | n-Hexanoate | A | 16[e] |
| 10 | 11 | n-Heptanoate | A | 1[e] |
| 11 | 12 | Benzoate | A | 9[e,f] |
| 12 | -- | n-Octanoate | A | 0 |
| 13 | -- | Trifluoroacetate | A | 0 |
| 14 | 13 | Succinate | B | 18[e] |
| 15 | 14 | Citrate | B | 24[e,g] |
| 16 | 15 | L-Malate | B | 12[e,g] |
| 17 | 16 | DL-Lactate | B | [g] |
| 18 | 17 | Glycolate | B | [g] | a) Reaction conditions: A- carboxylic acid, $Na_2CO_3$, NAD, 90 °C; B- carboxylic acid, pyridine, NAD, 90 °C. See supporting information for details. b) Combined yield of 2' and 3' isomers. c) isolated yield following ion chromatography and desalting. d) mass recovery before chromatography, includes 10% NAD e) isolated yield following HPLC purification (C-18 column). f) 1', 2', and 3' isomers were isolated. g) Mixture of carboxylate regioisomers g) Product mixture contained mainly ADPribose.

US 9,376,461 B2

NON-ENZYMATIC SYNTHESIS OF O-ACETYL-ADP-RIBOSE AND ANALOGUES THEREOF

This application is the US National Stage of International Application No. PCT/US2012/041053, filed 6 Jun. 2012, which is incorporated herein by reference. This application also claims benefit of the filing date of U.S. 61/493,677 filed 6 Jun. 2011.

BACKGROUND

The sirtuins are an evolutionarily ancient class of enzymes present in all organisms from prokaryotes to humans (Sauve (2010) *Biochim. Biophys. Acta* 1804: 1591). One demonstrated function of these enzymes is protein deacylation. Sirtuins are capable of deacylating many different proteins, but the process is absolutely dependent on nicotinamide adenine dinucleotide (NAD), and the common products of all sirtuin mediated deacylation reactions are nicotinamide and O-acetyl-adenosine diphosphate ribose (OAADPR). While nicotinamide is involved in many different biological reactions, biosynthesis of OAADPR is only known to occur via sirtuin mediated protein deacylation (Tanner et al. (2000) *Proc. Natl. Acad. Sci. USA* 97: 14178; Tong and Denu (2010) *Biochem. Biophys. Acta* 1804: 1617; Lee et al. (2008) *Anal. Biochem.* 383: 174).

There is evidence that OAADPR, presumably as the mixture of 2' and 3' isomers, functions as an intracellular second messenger (Wolberger and Hoff (2005) *Nat. Struct. Mol. Biol.* 12: 560). Microinjection experiments showed that starfish oocyte maturation could be delayed or halted by infusion of OAADPR (Borra et al. (2002) *J. Biol. Chem.* 277: 12632). Several intracellular proteins have been shown to bind OAADPR, and mechanisms for the regulation of gene transcription have been proposed (Norris and Boeke (2010) *Genes Dev.* 24: 115). Additionally, enzymes that catalyze the degradation of OAADPR are known (Ono et al. (2006) *Proc. Natl. Acad. Sci. USA* 103: 16687). The identification of additional proteins that interact with OAADPR is an area of active investigation (Tanner et al. (2000) *Proc. Natl. Acad. Sci. USA* 97: 14178).

Previously, three groups prepared isolable amounts of OAADPR. Schramm et al. performed an acyl transfer from an 18 amino acid peptide bearing a $N_\epsilon$-acetyllysine residue to NAD using a bacterial sirtuin enzyme as the catalyst (Sauve et al. (2001) *Biochemistry* 40: 15456). Borra and Denu used a similar enzymatic approach to prepare OAADPR, employing a *Drosophila* sirtuin as the catalyst, while Moss used human SIRT1 as the catalyst (Borra et al. (2002) *J. Biol. Chem.* 277: 12632; Ono et al. (2006) *Proc. Natl. Acad. Sci. USA* 103: 16687). Comstock and Denu performed the first total synthesis of OAADPR using a 12-step sequence that allowed them to prepare a mixture of 2'-O-acetyl-ADP ribose and 3'-O-acetyl-ADP ribose isomers, as well as several amide isosteres (Comstock and Denu (2007) *Org. Biomol. Chem.* 5: 3087). Denu and Schramm both showed that the regioisomers 2'-O-acetyl-ADP ribose and 3'-O-acetyl-ADP ribose interconverted in aqueous solution at pH=7.5, giving a 1:1 ratio of regioisomers at equilibrium (Jackson and Denu (2002) *J. Biol. Chem.* 277: 18535).

The use of a sirtuin catalyzed biochemical reaction to generate OAADPR requires enzymatically active sirtuin preparations and is commensurately limited in scale and economy. The efficient preparation of OAADPR from readily available starting materials using a simple, inexpensive, and easily scaled chemical synthetic method would provide an improved method of producing this compound for its multiple uses in biotechnology and the biological arts.

BRIEF DESCRIPTION OF THE FIGURES

FIG. 10 shows ADP-ribose esters synthesized from NAD and carboxylates.

SUMMARY

Figure 3:
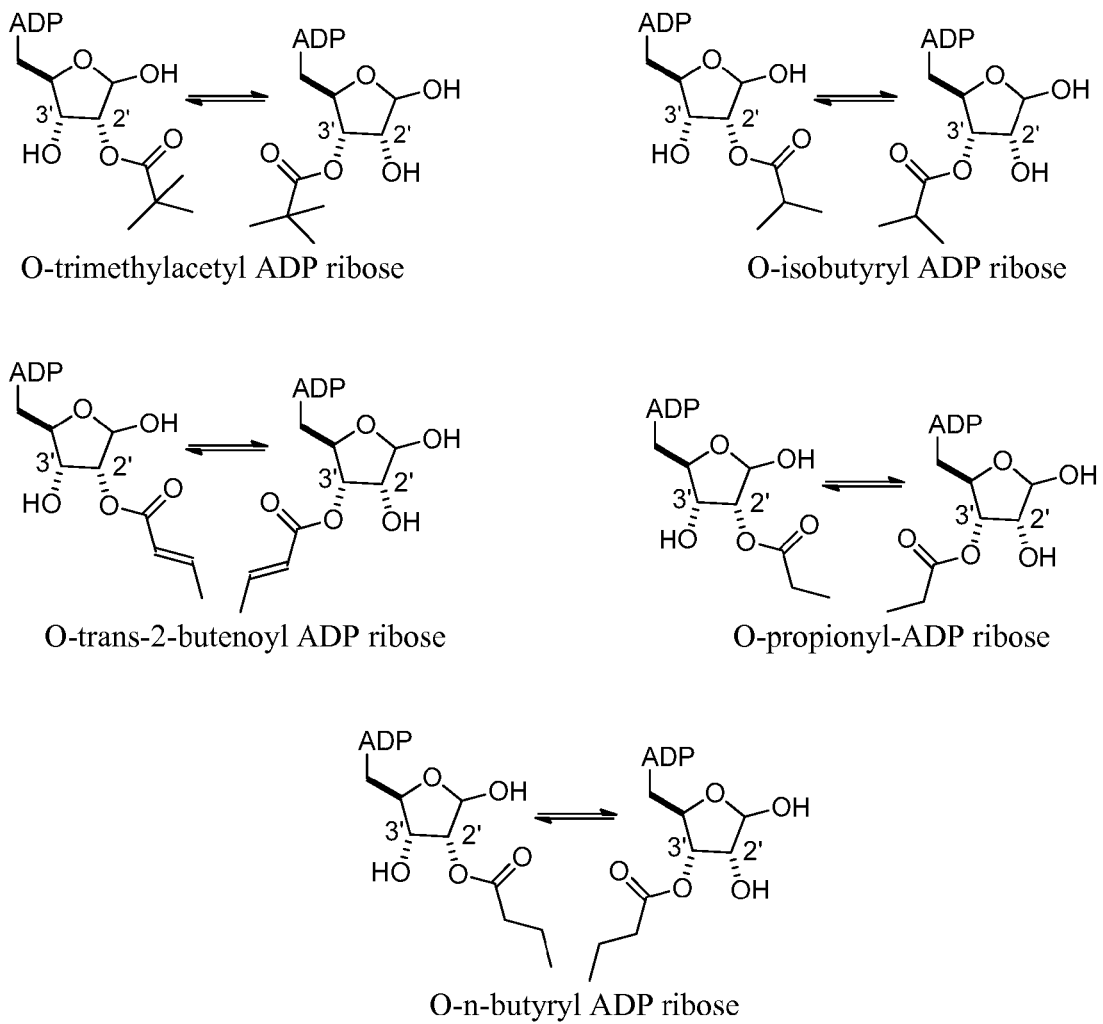
FIG. 3 shows novel compositions of O-carboxylated nucleoside diphosphate ribose esters.

The invention is based, in part, upon the discovery of a novel non-enzymatic method of synthesizing OAADPR, a naturally-occurring product of the NAD-dependent deacetylation of acetylated proteins by the sirtuins, which are members of the class III histone deacetylases. The reaction is general for carboxylic acids and NAD and can be used to prepare ester analogues of OAADPR, as well as deuterated OAADPR analogs. Accordingly, the invention further provides novel methods for synthesizing other (non-acetyl) carboxylated analogs of OAADPR and/or other (non-adenosine) nucleoside analogs of OAADPR, as well as associated novel compositions of O-carboxylated nucleoside diphosphate ribose including O-trimethylacetyl ADP ribose, O-isobutyryl ADP ribose, and O-trans-2-butenoyl ADP ribose, novel compositions comprising purified O-propionyl-ADP ribose and O-n-butyryl ADP ribose, among others (e.g., see FIG. 3).

In one aspect, the invention provide a non-enzymatic method for synthesizing an O-carboxyl ester of adenosine diphosphate ribose (ADP-ribose) or a non-adenosine nucleoside diphosphate ribose (NDP-ribose) analog thereof (III). The method includes the step of reacting a carboxylate (II) with NAD, or an analog thereof having an ADP or NDP nucleoside, and a nicotinamide or a non-nicotinamide leaving group (LG) (I) as shown below. This reaction produces an O-carboxyl-ADP/NDP ribose product (III). The O-carboxyl-ADP/NDP ribose product (III, wherein one of $R_1$ and $R_2$ is H, and the other is —C(O)—$R_x$) is a mixture of 2'-O-carboxyl-ADP/NDP-ribose (III a, wherein $R_1$ is H and $R_2$ is —C(O)—$R_x$) and 3'-O-carboxyl-ADP/NDP-ribose (III b, wherein $R_1$ is —C(O)—$R_x$ and $R_2$ is H) products, as shown below, where $R_x$ may be an optionally substituted $C_1$-$C_{12}$ straight or branched alkyl or alkene, or an optionally substituted carbocycle or heterocycle.

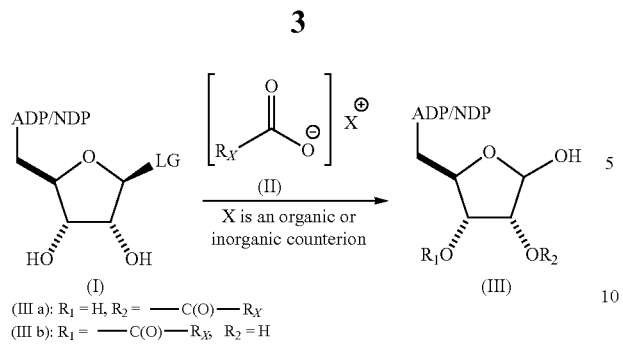

(III a): R₁ = H, R₂ = —C(O)—R$_X$
(III b): R₁ = —C(O)—R$_X$, R₂ = H

In select embodiments, (I) is NAD. In further select embodiments, the carboxylate (II) is acetate and the product is OAADPR.

Figure 4:
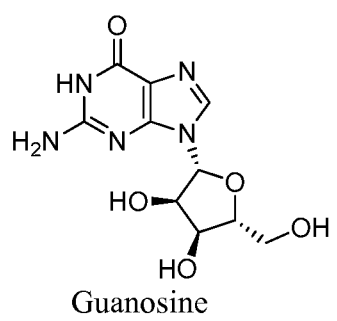
FIG. 4 shows non-adenosine (NDP) nucleoside diphosphates.
Figure 4:
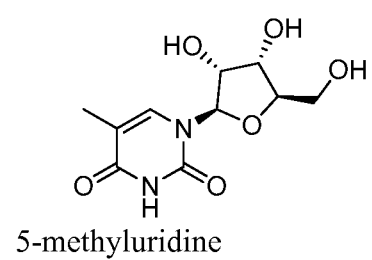
Figure 4:
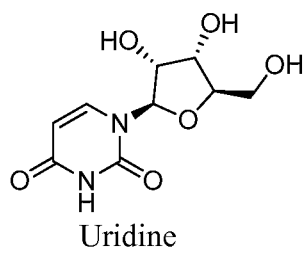
Figure 4:
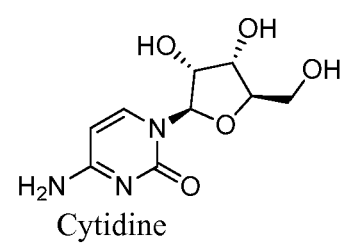

In certain embodiments of this method of the invention, the dinucleotide is comprised of a nicotinamide or non-nicotinamide LG and a non-adenosine nucleoside-containing analog of NAD having a guanosine, 5-methyluridine, uridine, or cytidine nucleoside in place of adenosine (e.g., see FIG. 4). In other embodiments, the carboxylate (II) is a non-acetate carboxylate such as propionate, n-butyrate, isobutyrate, trimethylacetate, trans-2-butenoate, n-pentanoate, 3,3-dimethylacrylate, n-hexanoate, n-heptanoate, benzoate, succinate, citrate, DL-lactate or L-malate (e.g., see corresponding carboxylic acids in FIG. 6).

Figure 5:
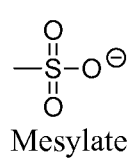
FIG. 5 shows non-NAD leaving groups.
Figure 5:
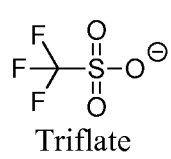
Figure 5:
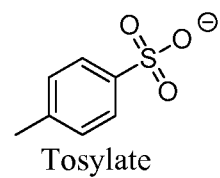
Figure 5:

In further embodiments, (I) is an analog of NAD having a LG, such as nicotinic acid or a halogen (e.g., Cl, Br, I, or F). In other embodiments, the LG is a good chemical leaving group such as methanesulfonate (mesylate), trifluoromethanesulfonate (triflate), toluenesulfonate (tosylate) or benzenesulfonate (besylate) (e.g., see FIG. 5). In further embodiments, the LG is a chemical moiety selected from the following:

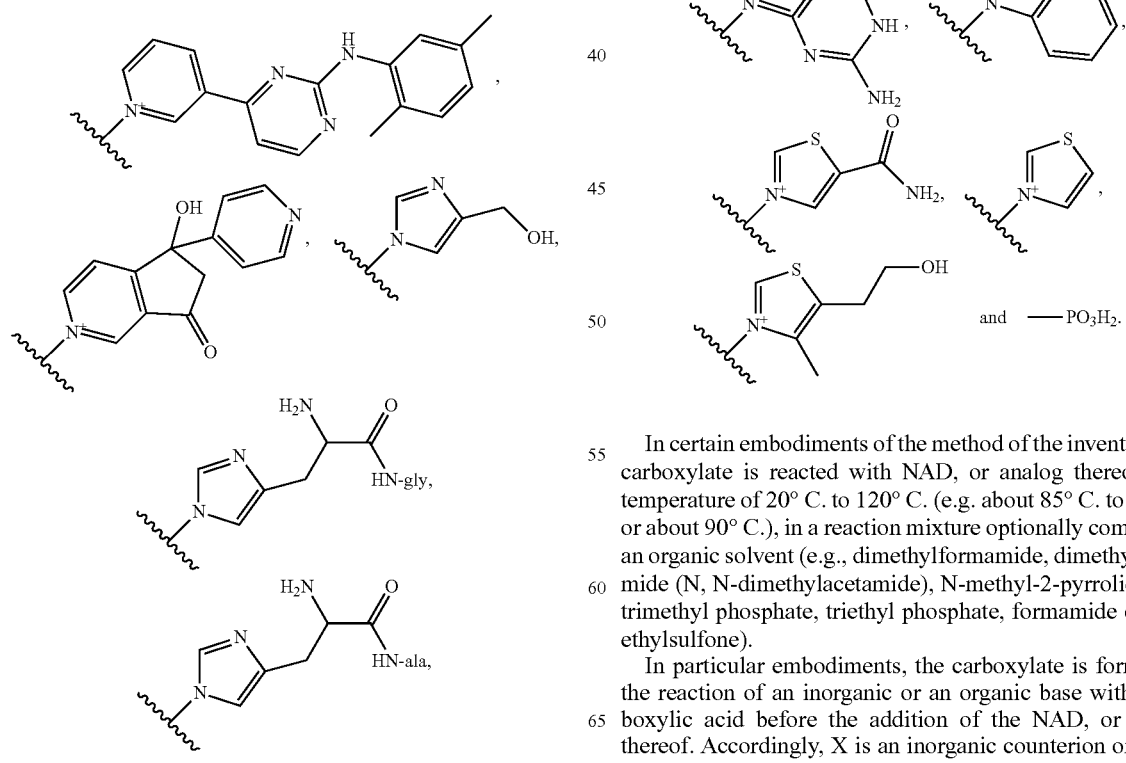

and —PO₃H₂.

In certain embodiments of the method of the invention, the carboxylate is reacted with NAD, or analog thereof, at a temperature of 20° C. to 120° C. (e.g. about 85° C. to 95° C., or about 90° C.), in a reaction mixture optionally comprising an organic solvent (e.g., dimethylformamide, dimethylacetamide (N, N-dimethylacetamide), N-methyl-2-pyrrolidinone, trimethyl phosphate, triethyl phosphate, formamide or dimethylsulfone).

In particular embodiments, the carboxylate is formed by the reaction of an inorganic or an organic base with a carboxylic acid before the addition of the NAD, or analog thereof. Accordingly, X is an inorganic counterion or a protonated organic base.

In some embodiments, the carboxylic acid is reacted with an inorganic base that is an alkali metal oxide or an alkaline earth metal oxide. In further embodiments, the inorganic base that is reacted with the carboxylic acid is an alkali metal or an alkaline earth metal. In particular embodiments, the inorganic base is an alkali metal carbonate, an alkali metal bicarbonate, an alkaline earth metal carbonate, or an alkaline earth metal bicarbonate (e.g., Na$_2$CO$_3$ or NaHCO$_3$) and X is an alkali metal or an alkaline earth metal counterion. In certain embodiments, the inorganic base is Na$_2$CO$_3$ (X is Na), the dinucleotide is NAD, and the carboxylic acid is acetic acid. In further embodiments, the inorganic base is Na$_2$CO$_3$ (X is Na), the dinucleotide is NAD, and the carboxylic acid is trimethylacetic acid, crotonic acid, 3,3-dimethylacrylic acid or benzoic acid (e.g., see FIG. 6).

In further embodiments, the carboxylate is formed by the reaction of a carboxylic acid with an organic base, such as a trialkylamine (e.g., trimethylamine or triethylamine), a 5 to 6-membered nitrogen containing heterocycle, or a (C$_1$-C$_4$ alkyl) substituted 5 to 6-membered nitrogen containing heterocycle and X is trialkylammonium (e.g., a trimethylammonium or triethylammonium counterion), a protonated 5 to 6-membered nitrogen containing heterocycle, or a protonated (C$_1$-C$_4$ alkyl) substituted 5 to 6-membered nitrogen containing heterocycle. In certain embodiments, the organic base is pyridine or imidazole (X is a pyridinium or an imidazolium counterion). In particular embodiments, the organic base is pyridine, the dinucleotide is NAD, and the carboxylic acid is succinic acid, citric acid, DL-lactic acid or L-malic acid.

Figure 6:
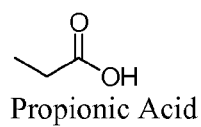
FIG. 6 shows carboxylic acids.
Figure 6:
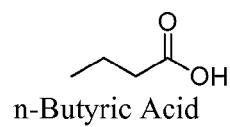
Figure 6:
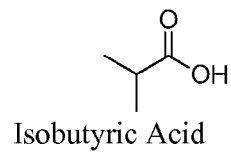
Figure 6:
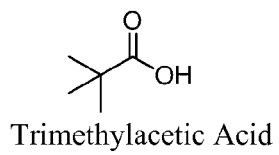
Figure 6:
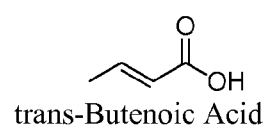
Figure 6:
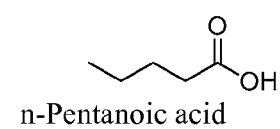
Figure 6:
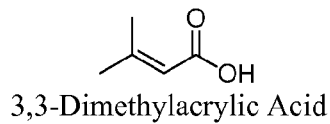
Figure 6:
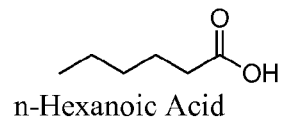
Figure 6:
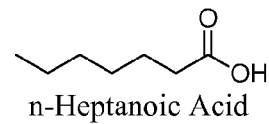
Figure 6:
Figure 6:
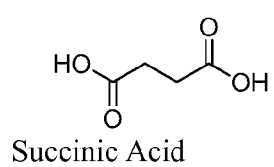
Figure 6:
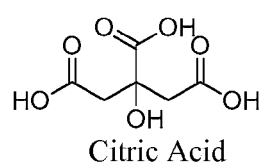
Figure 6:
Figure 6:
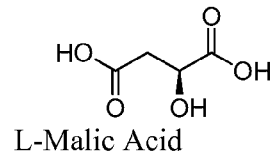
Figure 7:
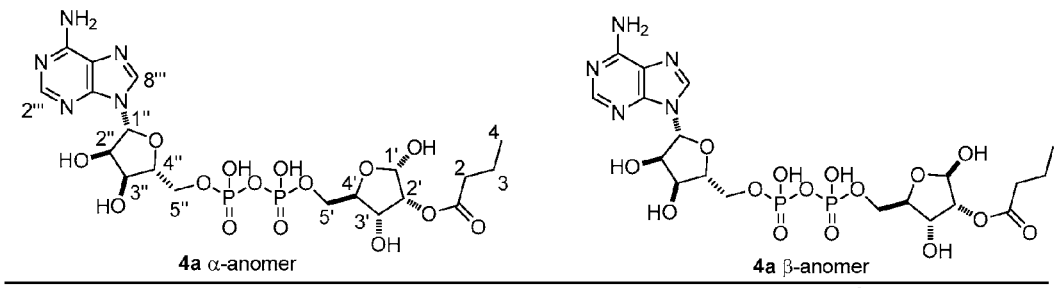
FIG. 7 shows H' NMR coupling constant and H' assignments for 2'-O-n-butyryl-ADP-ribose.
Figure 8:
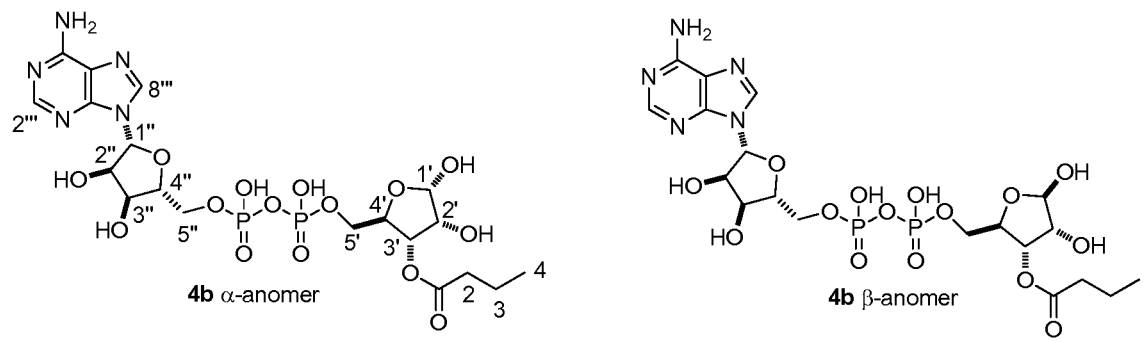
FIG. 8 shows H' NMR coupling constant and H' assignments NMR for 3'-butyryl-ADP-ribose.
Figure 9:
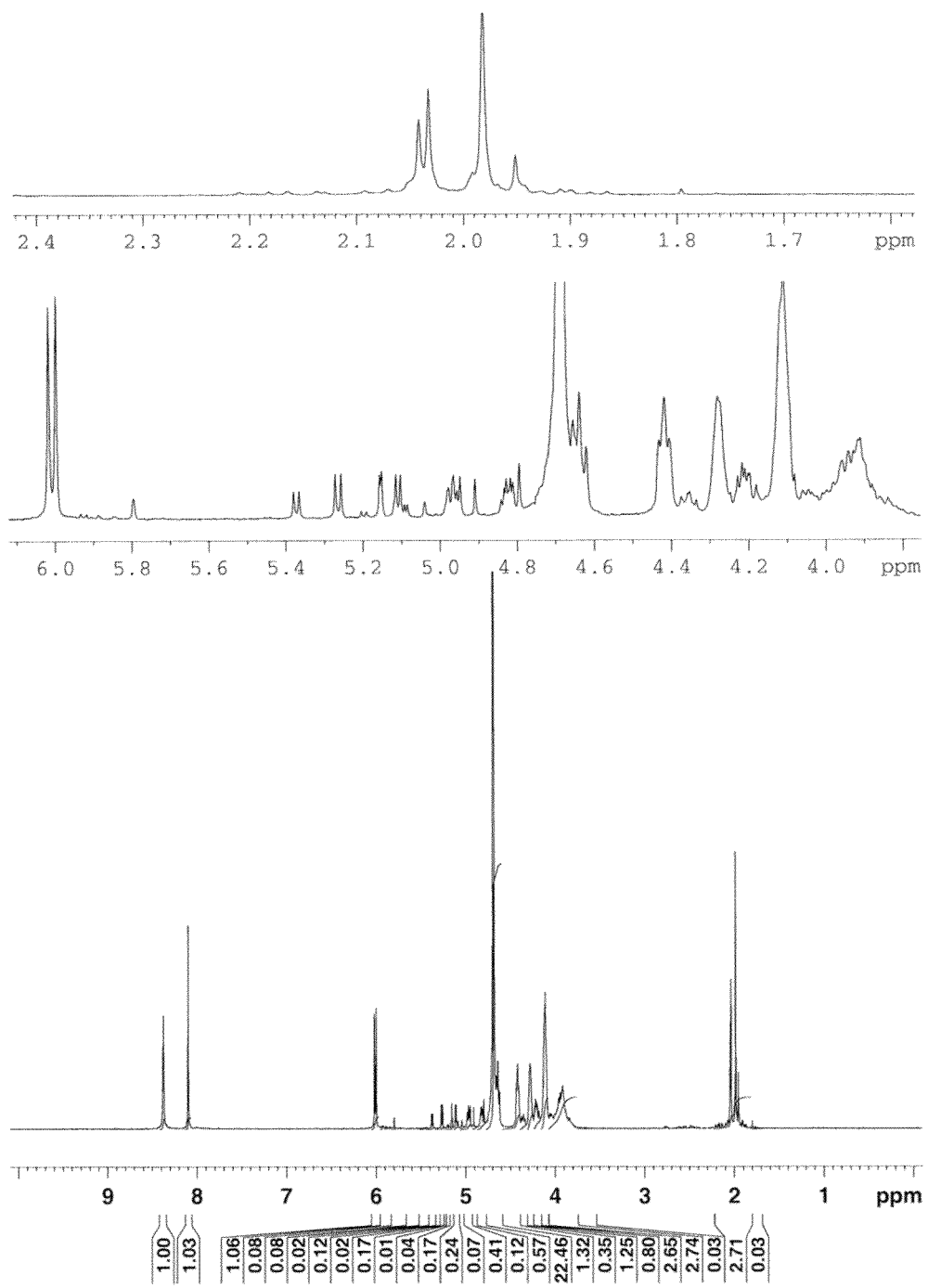
FIG. 9 shows H' NMR of a mixture of 2'- and 3'-O-acetyl-ADP ribose.

In still further embodiments of the method of the invention, the carboxylate is formed by the reaction of a base with a carboxylic acid such as propionic acid, n-butyric acid, isobutyric acid, trimethyl acetic acid, trans-butenoic acid, n-pentanoic acid, 3,3-dimethylacrylic acid, n-hexanoic acid, n-heptanoic acid, benzoic acid, succinic acid, citric acid, DL-lactic acid, or L-malic acid (e.g., see FIG. 6). In other embodiments, the carboxylate corresponds to a salt of one or more of these carboxylic acids. In particular embodiments, the carboxylic acid is acetic acid.

In further embodiments of this method of the invention, the method further includes the step of purifying the product (e.g., by ion chromatography to remove byproducts and other reaction components). In particular embodiments, the additional ion chromatography purification step is performed on an aminopropyl functionalized silica gel column. In certain embodiments, the additional ion chromatography purification step is performed on a strong cation exchange column. In particular embodiments, the strong cation exchange column is a benzenesulfonic acid linked silica gel column.

In another aspect, the invention provides a non-enzymatic method for synthesizing an O-carboxyl ester of ADP-ribose (III). The method includes the step of reacting a carboxylate (II) with NAD, or an analog thereof, having a nicotinamide or a nicotinic acid leaving group (Y), as shown below. This reaction produces an O-carboxyl-ADP-ribose product (III). The O-carboxyl-ADP-ribose product (III, wherein one of R$_1$ and R$_2$ is H, and the other is —C(O)—R$_x$) that is a mixture of 2'-O-carboxy-ADP-ribose (III a, wherein R$_1$ is H and R$_2$ is —C(O)—R$_x$) and 3'-O-carboxyl-ADP-ribose (III b, wherein R$_1$ is —C(O)—R$_x$ and R$_2$ is H) products, as shown below, where R$_x$ may be an optionally substituted C$_1$-C$_{12}$ straight or branched alkyl or alkene, or an optionally substituted carbocycle or heterocycle.

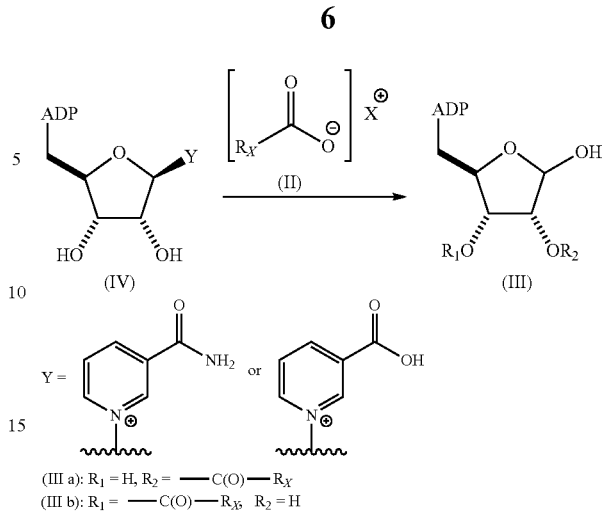

In select embodiments, Y is nicotinamide. In further select embodiments, Y is nicotinic acid.

In certain embodiments of this method of invention, the carboxylate is acetate and the product is O-acetyl-ADP ribose comprising a mixture of 2'-O-acetyl-ADP-ribose and 3'-O-acetyl-ADP-ribose. In other embodiments, the carboxylate (II) is selected from the group consisting of propionate, n-butyrate, isobutyrate, trimethyl acetate, trans-2-butenoate, n-pentanoate, 3,3-dimethylacrylate, n-hexanoate, n-heptanoate, benzoate, succinate, citrate, DL-lactate and L-malate.

In some embodiments, the carboxylate is reacted with the nicotinamide NAD, or analog thereof, at a temperature of 20° C. to 120° C. (e.g. about 85° C. to 95° C., or about 90° C.) in a reaction mixture optionally comprising an organic solvent (e.g., dimethylformamide, dimethylacetamide (N, N-dimethylacetamide), N-methyl-2-pyrrolidinone, trimethyl phosphate, triethyl phosphate, formamide or dimethylsulfone). In further embodiments, the carboxylate is formed by the reaction of an inorganic or organic base with a carboxylic acid before the addition of NAD, or analog thereof.

In certain embodiments, the carboxylic acid is reacted with an inorganic base. In further embodiments, the inorganic base that is reacted with the carboxylic acid is an alkali metal or an alkaline earth metal. In particular embodiments, the inorganic base is alkali metal carbonate, an alkali metal bicarbonate, an alkaline earth metal carbonate, or an alkaline earth metal bicarbonate (e.g., Na$_2$CO$_3$ or NaHCO$_3$). In certain embodiments, the inorganic base is Na$_2$CO$_3$, the dinucleotide is NAD, and the carboxylic acid is acetic acid. In further embodiments, the inorganic base is Na$_2$CO$_3$, the dinucleotide is NAD, and the carboxylic acid is trimethylacetic acid, crotonic acid, 3,3-dimethylacrylic acid or benzoic acid.

In further embodiments, the carboxylate is formed by the reaction of a carboxylic acid with an organic base, such as a trialkylamine (e.g., trimethylamine or triethylamine), a 5 to 6-membered nitrogen containing heterocycle, or an optionally C$_1$-C$_4$ substituted 5 to 6-membered nitrogen containing heterocycle. In certain embodiments, the organic base is pyridine or imidazole. In particular embodiments, the organic base is pyridine, the dinucleotide is NAD and the carboxylic acid is succinic acid, citric acid, DL-lactic acid or L-malic acid.

In still further embodiments of the method of the invention, the carboxylate is formed by the reaction of a base with a carboxylic acid such as propionic acid, n-butyric acid, isobutyric acid, trimethyl acetic acid, trans-butenoic acid, n-pentanoic acid, 3,3-dimethylacrylic acid, n-hexanoic acid, n-heptanoic acid, benzoic acid, succinic acid, citric acid, DL-lactic acid, or L-malic acid. In other embodiments, the carboxylate corresponds to a salt of one or more of these carboxylic acids. In particular embodiments the carboxylic acid is acetic acid.

In further embodiments of this method of the invention, the method further includes the step of purifying the product (e.g., by ion chromatography to remove byproducts and other reaction components). In particular embodiments, the additional ion chromatography purification step is performed on an aminopropyl functionalized silica gel column. In certain embodiments, the additional ion chromatography purification step is performed on a strong cation exchange column. In particular embodiments, the strong cation exchange column is a benzenesulfonic acid linked silica gel column.

In still another aspect, the invention provides a non-enzymatic method for synthesizing an O-acetyl ester of ADP-ribose (VII). The method includes the step of reacting NAD (V) with acetic acid (VI). In the presence of an organic or inorganic base, this reaction produces an O-acetyl-ADP-ribose product (VII). The O-acetyl-ADP-ribose product (VII, wherein one of $R_3$ and $R_4$ is H, and the other is —C(O)—$CH_3$), is a mixture of 2'-O-acetyl-ADP-ribose (VII a, wherein $R_3$ is H and $R_4$ is —C(O)—$CH_3$) and 3'-O-acetyl-ADP-ribose (VII b, wherein $R_1$ is —C(O)—$CH_3$ and $R_2$ is H), as shown below.

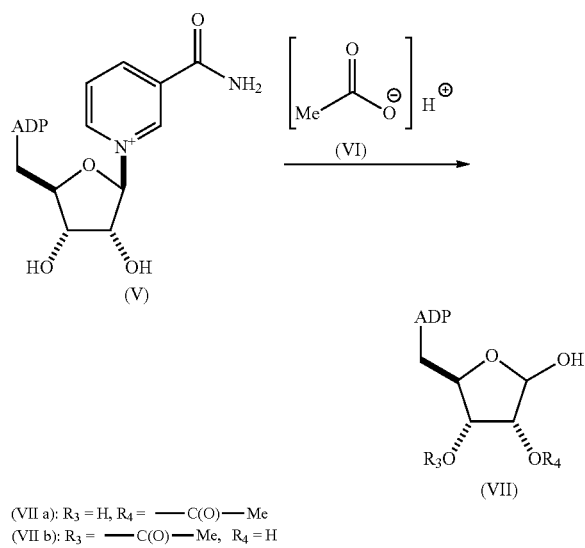

(VII a): $R_3$ = H, $R_4$ = —C(O)—Me
(VII b): $R_3$ = —C(O)—Me, $R_4$ = H

In particular embodiments, the methyl groups of products (VII a and VII b) are deuterated.

In select embodiments, sodium acetate is reacted with NAD at a temperature of 20° C. to 120° C. (e.g., about 85° C. to 95° C., or about 90° C.) in a reaction mixture optionally comprising an organic solvent (e.g., dimethylformamide, dimethylacetamide (N, N-dimethylacetamide), N-methyl-2-pyrrolidinone, trimethyl phosphate, triethyl phosphate, formamide or dimethylsulfone). In further embodiments, sodium acetate is formed by the reaction of $Na_2CO_3$ with acetic acid before the addition of the NAD.

In further embodiments of this method of the invention, the method further includes the step of purifying the product (e.g., by ion chromatography to remove byproducts and other reaction components). In particular embodiments, the additional ion chromatography purification step is performed on an aminopropyl functionalized silica gel column. In certain embodiments, the additional ion chromatography purification step is performed on a strong cation exchange column. In particular embodiments, the strong cation exchange column is a benzenesulfonic acid linked silica gel column.

In yet another aspect, the invention provides O-carboxyl ester of ADP/NDP-ribose represented by Structural Formula (VIII, wherein one of $R_5$ and $R_6$ is H and the other is a Carboxyl, e.g. —C(O)—$R_x$):

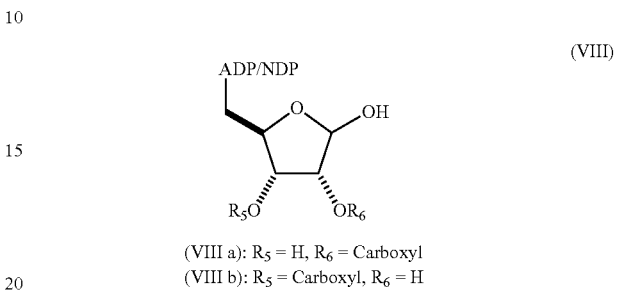

(VIII a): $R_5$ = H, $R_6$ = Carboxyl
(VIII b): $R_5$ = Carboxyl, $R_6$ = H

The compounds are made up of a mixture of 2'-O-carboxyl-ADP/NDP-ribose (VIII a, wherein $R_5$ is H and $R_6$ is a Carboxyl represented by the formula —C(O)—$R_x$) and 3'-O-carboxyl-ADP/NDP-ribose (VIII b, wherein $R_5$ is a Carboxyl represented by the formula —C(O)—$R_x$ and $R_6$ is a H), where $R_x$ is an optionally substituted $C_4$-$C_{12}$ straight or branched alkyl or alkene, or an optionally substituted carbocycle or heterocycle. Exemplary "Carboxyl" moieties include —C(O)—($C_4$-$C_6$)alkyl, —C(O)—CH(OH)—($C_1$-$C_3$ alkyl), —C(O)—($C_1$-$C_3$)alkyl-COOR', —C(O)—($C_1$-$C_3$)alkyl-C(OR')(COOR')—($C_1$-$C_3$)alkyl-COOR'), —C(O)—CH(OR')—COOR', —C(O)—CR'—($CH_3$)$_2$, —C(O)—CR'=CR—($C_1$-$C_3$ alkyl), —C(O)—CR'=C($CH_3$)$_2$ and —C(O)-carbocycle, where each R' is independently selected from H and optionally substituted $C_1$-$C_3$ alkyl.

In certain embodiments the nucleoside is adenosine. In other embodiments, the nucleoside is a non-adenosine nucleoside such as a guanosine, 5-methyluridine, uridine, or cytidine nucleoside.

In further embodiments, one of $R_5$ and $R_6$ is H, and the other is selected from the group consisting of C(O)—CH—($CH_3$)$_2$ (ester of isobutyrate), —C(O)—C($CH_3$)$_3$ (ester of trimethylacetate), —C(O)—CH=CH—$CH_3$ (ester of trans-2-butenoate), —C(O)—$CH_2$—$CH_2$—$CH_2$—$CH_3$ (ester of n-pentanoate), —C(O)—CH=C($CH_3$)$_2$ (ester of 3,3,-dimethylacrylate), —C(O)—($CH_2$)$_4$—$CH_3$ (ester of n-hexanoate), —C(O)—($CH_2$)$_5$—$CH_3$ (ester of n-heptanoate), —C(O)—$C_6H_5$ (ester of benzoate), —C(O)—($CH_2$)$_2$—C(O)—OH, (ester of succinate), —C(O)—$CH_2$—C(OH)(COOH)—$CH_2$—COOH (ester of citrate), —C(O)—CH(OH)—$CH_3$ (ester of DL-lactate) and —C(O)—CH(OH)—$CH_2$—COOH (ester of L-malate).

In a related aspect, the invention includes O-carboxyl esters of NDP-ribose having the same general structure (VIII) above, but where one of $R_5$ and $R_6$ is H, and the other is a "Carboxyl" —C(O)—$R_x$ moiety, and the $R_x$ is an optionally substituted $C_1$-$C_3$ straight or branched alkyl or alkene, or an optionally substituted carbocycle. Included in this aspect of the invention are exemplary "Carboxyl" moieties of the structure: —C(O)—($C_1$-$C_3$)alkyl groups (e.g., O-acetyl-NDP-ribose, O-propionyl-NDP-ribose, O-n-butyryl-NDP-ribose, and O-isobutyryl-NDP-ribose).

In still further embodiments of these compounds, the invention provides the above compounds (e.g., occurring as a mixture of 2'-O-carboxyl-ADP/NDP-ribose (VIII a) and 3'-O-carboxyl-ADP/NDP-ribose (VIII b) in a form that is isolated to 90% to 99% molar purity (e.g., 90% molar purity, 95% molar purity, or 99% molar purity). In the alternative, the purity of the compounds of the invention may be 90% to 99% pure (i.e., free from contaminating non-solvent matter) on a weight/weight (w/w) basis (e.g., 90% w/w pure, 95% w/w pure, or 99% w/w pure).

In yet another aspect, the invention provides an isolated O-propionyl ester of ADP/NDP-ribose represented by Structural Formula (IX, wherein one of $R_7$ and $R_8$ is H and the other is $-C(O)-CH_2-CH_3$):

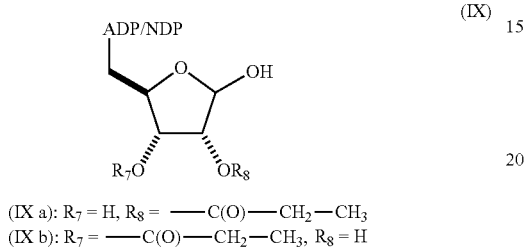

(IX a): $R_7$ = H, $R_8$ = $-C(O)-CH_2-CH_3$
(IX b): $R_7$ = $-C(O)-CH_2-CH_3$, $R_8$ = H

These compounds of the invention are made up of a mixture of 2'-O-propionyl-ADP/NDP-ribose (IX a, wherein $R_7$ is H and $R_8$ is $-C(O)-CH_2-CH_3$) and 3'-O-propionyl-ADP/NDP-ribose (IX b, wherein $R_7$ is $-C(O)-CH_2-CH_3$ and $R_8$ is H), wherein one of $R_7$ and $R_8$ is H, and the other is $-C(O)-CH_2-CH_3$, and the isolated O-propionyl ester of ADP-ribose is isolated to at least 90% molar purity.

In certain embodiments a mixture of 2'-O-propionyl-ADP/NDP-ribose (IX a) and 3'-O-propionyl-ADP/NDP-ribose (IX b) is isolated to 90% to 99% molar purity (e.g., 90% molar purity, 95% molar purity, or 99% molar purity). In the alternative, the purity of these compounds of the invention may be 90% to 99% pure (i.e., free from contaminating non-solvent matter) on a weight/weight (w/w) basis (e.g., 90% w/w pure, 95% w/w pure, or 99% w/w pure).

In yet another aspect, the invention provides an isolated O-n-butyryl ester of ADP/NDP-ribose) represented by Structural Formula (X, wherein one of $R_9$ and $R_{10}$ is H and the other is $-C(O)-(CH_2)_2-CH_3$):

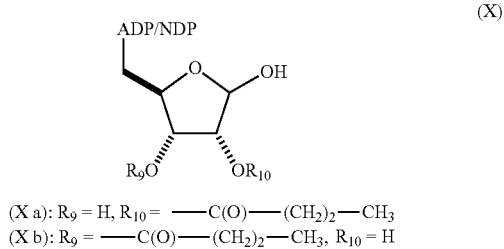

(X a): $R_9$ = H, $R_{10}$ = $-C(O)-(CH_2)_2-CH_3$
(X b): $R_9$ = $-C(O)-(CH_2)_2-CH_3$, $R_{10}$ = H comprising a mixture of 2'-O-n-butyryl-ADP/NDP-ribose (X a, wherein $R_9$ is H and $R_{10}$ is $-C(O)-(CH_2)_2-CH_3$) and 3'-O-n-butyryl-ADP/NDP-ribose (X b, wherein $R_9$ is $-C(O)-(CH_2)_2-CH_3$ and $R_{10}$ is H), wherein one of $R_9$ and $R_{10}$ is H, and the other is $-C(O)-(CH_2)_2-CH_3$, and the isolated compound is isolated to at least 90% molar purity.

In certain embodiments a mixture of 2'-O-propionyl-ADP/NDP-ribose (X a) and 3'-O-propionyl-ADP/NDP-ribose (X b) is isolated to 90% to 99% molar purity (e.g., 90% molar purity, 95% molar purity, or 99% molar purity). In the alternative, the purity of these compounds of the invention may be 90% to 99% pure (i.e., free from contaminating non-solvent matter) on a weight/weight (w/w) basis (e.g., 90% w/w pure, 95% w/w pure, or 99% w/w pure).

In still another aspect, the invention provides methyl deuterated OAADPR represented by structural formula XI wherein one of $R_{11}$ and $R_{12}$ is H and the other is $-C(O)-CD_3$:

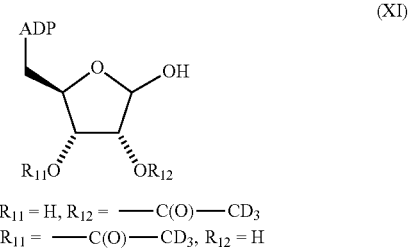

(XI a): $R_{11}$ = H, $R_{12}$ = $-C(O)-CD_3$
(XI b): $R_{11}$ = $-C(O)-CD_3$, $R_{12}$ = H comprising a mixture of 2'-O-deuterated acetyl-ADP-ribose (XI a, wherein $R_{11}$ is H and $R_{12}$ is $-C(O)-CD_3$) and 3'-O-deuterated acetyl-ADP-ribose (XI b, wherein $R_{11}$ is $-C(O)-CD_3$ and $R_{12}$ is H).

In certain embodiments, the compound of the invention is selected from any one of Compound Numbers 2, 3, 4, 5, 6, 7, 8, 9, 10, 11, 12, 13, 14, 15, 16, 17 (Table 1, FIG. 10) and deuterated OAADPR.

DETAILED DESCRIPTION

1. Definitions

As used herein, the following terms and phrases shall have the meanings set forth below. Unless defined otherwise, all technical and scientific terms used herein have the same meaning as commonly understood to one of ordinary skill in the art.

As used herein, a compound or composition of a stated percent "purity" means that compound or composition is chemically enriched to the stated molar purity over other contaminating compounds (e.g., as might be achieved by chemical synthesis or by identification and isolation from a natural source).

A "patient", "subject", "individual" or "host" refers to either a human or a non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pyrogen-free", with reference to a composition, refers to a composition that does not contain a pyrogen in an amount that would lead to an adverse effect (e.g., irritation, fever, inflammation, diarrhea, respiratory distress, endotoxic shock, etc.) in a subject to which the composition has been administered. For example, the term is meant to encompass compositions that are free of, or substantially free of, an endotoxin such as, for example, a lipopolysaccharide (LPS).

"Sirtuin-activating compound" refers to a compound that increases the level of a sirtuin protein and/or increases at least one activity of a sirtuin protein. In an exemplary embodiment, a sirtuin-activating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

"Sirtuin protein" refers to a member of the sirtuin deacetylase protein family, or preferably to the sir2 family, which include yeast Sir2 (GenBank Accession No. P53685), C. elegans Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

"SIRT1 protein" refers to a member of the sir2 family of sirtuin deacetylases. In one embodiment, a SIRT1 protein includes yeast Sir2 (GenBank Accession No. P53685), C. elegans Sir-2.1 (GenBank Accession No. NP_501912), human SIRT1 (GenBank Accession No. NM_012238 or NP_036370 (or AF083106)), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein", "SIRT3 protein", "SIRT4 protein", SIRT 5 protein", "SIRT6 protein", and "SIRT7 protein" refer to other mammalian, e.g. human, sirtuin deacetylase proteins that are homologous to SIRT1 protein, particularly in the approximately 275 amino acid conserved catalytic domain. For example, "SIRT3 protein" refers to a member of the sirtuin deacetylase protein family that is homologous to SIRT1 protein. In one embodiment, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In one embodiment, a SIRT3 protein includes a fragment of SIRT3 protein that is produced by cleavage with a mitochondrial matrix processing peptidase (MPP) and/or a mitochondrial intermediate peptidase (MIP).

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The compounds and salts thereof described herein can also be present as the corresponding hydrates (e.g., hemihydrate, monohydrate, dihydrate, trihydrate, tetrahydrate) and solvates. Suitable solvents for preparation of solvates and hydrates can generally be selected by a skilled artisan.

The compounds and salts thereof can be present in amorphous or crystalline (including co-crystalline and polymorphic) forms.

The term "non-enzymatic," as used herein, refers to a reaction that is not catalyzed by an enzyme.

The term "substituted," as used herein, refers to a group in which one or more hydrogen atoms are each independently replaced with the same or different substituent(s). Typical substituents include, but are not limited to a halogen, alkyl, substituted alkyl, amine, substituted amine, hydroxyl, substituted hydroxyl, O-alkyl, substituted O-alkyl, N-alkyl, substituted N-alkyl, aryl, substituted aryl, arylalkyl, substituted arylalkyl, cycloalkyl, substituted cycloalkyl, cycloheteroalkyl, substituted cycloheteroalkyl, cycloheteroalkyldiyl, substituted cycloheteroalkyldiyl, heteroalkyl, substituted heteroalkyl, heteroaryl, substituted heteroaryl, heteroarylalkyl, substituted heteroarylalkyl, substituted cycloheteroalkyl ring and the like.

The term, "isolated," as used herein, refers to a compound or compounds distinguished by a relative level of purity, e.g., by the separation of the pure chemical compound from a reaction or other mixture in which it occurs. For example, the isolation of a mixture of isomers results in a sample that is enriched to at least 90% molar purity, 95% molar purity or 99% molar purity as determined by standard spectroscopic methods e.g., H' NMR and LCMS. An isolated compound having at least 90% molar purity is one in which less than 10% or less of the non-solvent molecules in the isolated preparation are other compounds.

In the alternative, an "isolated" compound may be represented on the basis of its purity from other compounds on a weight or mass basis (e.g., a 90% w/w pure compound is a relatively isolated compound in which 10% or less of the non-solvent mass is due to other compounds). Accordingly, an isolated compound may be, for example, 90% w/w, 95% w/w, or 99% w/w.

The term "ion chromatography," also known as ion-exchange chromatography, is any form of chromatography that depends on the process of ion exchange to effect the separation.

The term "ion-exchanges" means the process in which ions of like charge, which may be the same or different chemically, are exchanged between two phases, such as a solution and an insoluble material, e.g. a resin.

The term "alkyl", as used herein, refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (—$CH_3$), ethyl (—$CH_2$—$CH_3$), ethyl ($CH_2$—$CH_3$), n-propyl (—$CH_2$—$CH_2$—$CH_3$), isopropyl (—$CH(CH_3)_2$), n-butyl (—$CH_2$—$CH_2$—$CH_2$—$CH_3$) and the like.

The term "alkene," as used herein refers to linear or branched-chain monovalent hydrocarbon radical of two to twelve carbon atoms with at least one site of unsaturation, (e.g., a carbon-carbon, $sp^2$ double bond), wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$—CH=$CH_2$) and the like.

The terms "carbocycle", and "carbocyclic", as used herein, refers to a saturated or unsaturated ring in which each atom of the ring is carbon. Carbocyclic includes 5-7 membered monocyclic and 8-12 membered bicyclic rings. Each ring of a bicyclic carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl and naphthyl.

A cycloalkyl group is a carbocycle which is completely saturated. Exemplary cycloalkyl groups include cyclopentyl, cyclohexyl, bicyclo[2,2,1]heptanyl and adamantyl.

The term "carboxylate," as used herein, refers to the conjugate base of a carboxylic acid ($RCOO^-$, where R is an organic group). It is an ion with a negative charge e.g. $^-$OOCH (formate), $^-$OOC$CH_3$(acetate), $^-$OOC—CH—$(CH_3)_2$ (isobutyrate), $^-$OOC—$C(CH_3)_3$ (trimethylacetate), $^-$OOC—CH=CH—$CH_3$ (trans-2-butenoate), $^-$OOC—$CH_2$—$CH_2$—$CH_2$—$CH_3$ (n-pentanoate), $^-$OOC—CH=$C(CH_3)_2$ (3,3,-dimethylacrylate), $^-$OOC—$(CH_2)_4$—$CH_3$ (n-hexanoate), $^-$OOC—$(CH_2)_5$—$CH_3$ (n-heptanoate), $^-$OOC—$C_6H_5$ (benzoate), $^-$OOC—$(CH_2)_2$—C(O)—OH, (succinate), $^-$OOC—$CH_2$—C(OH)(COOH)—$CH_2$—COOH (citrate), $^-$OOC—CH(OH)—$CH_3$ (DL-lactate), $^-$OOC—CH(OH)—$CH_2$—COOH (L-malate) and the like.

The terms "heterocycle", and "heterocyclic", as used herein, refers to a saturated or unsaturated ring comprising one or more heteroatoms selected from, for example, N, O, and S atoms. Heterocycles include 4-7 membered monocyclic and 8-12 membered bicyclic rings. Each ring of a bicyclic heterocycle may be selected from saturated, unsaturated and aromatic rings. In an exemplary embodiment, an aromatic ring, e.g., pyridyl, may be fused to a saturated or unsaturated ring, e.g., cyclohexane, cyclopentane, or cyclohexene. The terms "heterocyclyl" and "heterocyclic" also include polycyclic ring systems having two or more cyclic rings in which two or more carbons or heteroatoms are common to two adjoining rings wherein at least one of the rings is heterocyclic, e.g., the other cyclic rings can be cycloalkyls, cycloalkenyls, cycloalkynyls, aryls, heteroaryls, and/or heterocycloalkyls. Heterocyclyl groups include, for example, piperidine, piperazine, pyrrolidine, morpholine, lactones, and lactams.

The term "heteroaryl" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons or heteroatoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "leaving group," as used herein has the meaning conventionally associated with it in synthetic organic chemistry, i.e., an atom or a group capable of being displaced by a nucleophile and includes halo (such as chloro, bromo and iodo), acyloxy (e.g., acetoxy), mesyloxy, tosyloxy, trifluoromethanesulfonyloxy, aryloxy (e.g., 2,4-dinitrophenoxy), methoxy, N,O-dimethylhydroxylamino, and the like.

Monocyclic rings include 5-7 membered aryl or heteroaryl, 3-7 membered cycloalkyl, and 5-7 membered non-aromatic heterocyclyl. Exemplary monocyclic groups include substituted or unsubstituted heterocycles or carbocycles such as thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, cyclohexyl, cyclopentyl, cyclopropyl, cyclobutyl, cycloheptanyl, azetidinyl, oxetanyl, thiiranyl, oxiranyl, aziridinyl, and thiomorpholinyl.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl.

Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

Azabicyclo refers to a bicyclic molecule that contains a nitrogen atom in the ring skeleton. The two rings of the bicycle may be fused, at two mutually bonded atoms, e.g., indole, across a sequence of atoms, e.g., azabicyclo[2.2.1]heptane, or at a single atom, e.g., spirocycle.

Bridged azabicyclo refers to a bicyclic molecule that contains a nitrogen atom and two fused rings wherein the fusion occurs across a sequence of atoms, i.e., bridgehead atoms. Bridged bicyclo compounds comprise at least one bridge of one or more atoms connecting two bridgehead atoms.

Fluoro-substituted includes from one fluoro substituent up to per-fluoro-substitution. Exemplary fluoro-substituted $C_1$-$C_2$ alkyl includes —$CFH_2$, $CF_2H$, —$CF_3$, —$CH_2CH_2F$, —$CH_2CHF_2$, —$CHFCH_3$, and —$CF_2CHF_2$. Per-fluoro-substituted $C_1$-$C_2$ alkyl, for example, includes —$CF_3$ and —$CF_2CF_3$.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

The compounds disclosed herein also include partially and fully deuterated variants. Structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays. In certain embodiments, deuterated variants may be used for kinetic studies. One of ordinary skill in the art can select the sites at which such deuterium atoms are present.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

2. Exemplary Uses

The invention provides a method for the facile non-enzymatic synthesis of ADP/NDP ribose esters directly from NAD or analogs thereof having an ADP or NDP nucleoside and a LG. The product mixtures obtained under abiotic conditions using acetate are identical to those isolated from sirtuin enzyme-mediated preparations, however the reaction is broadly applicable to NAD or analogs thereof, and carboxylates other than acetate. This simple transformation makes OAADRP and other ADP/NDP ribose esters readily accessible compounds. The availability of the methods and associated products of the invention will greatly facilitate the study of the sirtuin deacetylases, e.g., their underlying enzymatic reaction mechanism, as well as their role in the regulation of biological pathways and in cellular and organismal function. In addition, the invention will facilitate the discovery of pharmacological modulators of sirtuin function by, for example, providing standardized references for the stoichiometric accumulation of sirtuin deacetylase-dependent OAADPR deacetylation products in assays for modulatory compounds and substances, as well as kits for performing these assays.

In particular, sirtuin deacetylases consume NAD and deacetylate Lys-Ac on an equimolar basis with OAADPR accumulation. Accordingly, OAADPR detection and quantification using various chromatographic (e.g., HPLC) and analytical (e.g., mass spectrometry) methodologies can be used to sensitively measure sirtuin deacetylase (e.g., SIRT1) activity. Therefore, the facile OAADPR production methods of the invention provide the means for establishing and performing sensitive and efficient sirtuin assays.

In addition, it has recently been discovered that certain proteins are also propionylated at lysine residues (e.g., histone H3 lysine 23 in mammalian cells (Liu, et al. (2009) *J. Biol. Chem.* 284: 32288) and can be depropionylated by the same sirtuin enzymes that deacetylate in a NAD-dependent manner. The invention provides means of facile synthesis of O-propionyl-ADP-ribose standards and therefore supports the means of assaying this reaction as well as detecting deproprionylation products in a biological sample. Furthermore, the detection and assay of still other post-translational carboxylation events that may exist in nature (e.g., butyrylation) are facilitated by the methods of the invention. For example, it has been reported that O-malonyl-ADP-ribose and O-succinyl-ADP-ribose are generated by SIRT5 (WO2012/006391).

The invention further provides a means for generating large amount of OAADPR, as well as related nucleoside analogs and other non-acetyl carboxyl analogs thereof, for the development of sirtuin-related therapeutics and diagnostics.

For example, large amounts of OAADPR are useful for the generation of antibodies that are immunologically specific to these compounds. Polycolonal antibodies to OAADPR or other ADP/NDP ribose esters of the invention can be prepared according to standard methods known in the art.

Monoclonal antibodies include hybrid and recombinant antibodies (e.g. "humanized" antibodies) regardless of species of origin or immunoglobulin class or subclass designation, as well as antibody fragments (e.g., Fab, F(ab')$_2$, and Fv), so long as they are capable of binding specifically to OAADPR or a related compound of the invention (Cabilly, et al., U.S. Pat. No. 4,816,567; Mage & Lamoyi, in Monoclonal Antibody Production Techniques and Applications, pp. 79-97 (Marcel Dekker, Inc., New York, 1987)). The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as being obtained from such a substantially homogeneous population of antibodies, and is not to be construed as requiring production of the antibody by any particular method. For example, the monoclonal antibodies of the invention may be made using the hybridoma method first described by Kohler & Milstein, Nature 256:495 (1975), or may be made by recombinant DNA methods (Cabilly, et al., U.S. Pat. No. 4,816, 567). In the hybridoma method, a mouse or other appropriate host animal is immunized with OAADPR or a related compound of the invention by subcutaneous, intraperitoneal, or intramuscular routes to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The invention further provides compounds that may be formulated into useful pharmaceutical compositions comprising a substantially purified OAADPR or a related compound of the invention in conjunction with a suitable pharmaceutical carrier. The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing, Easton, Pa.). Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

Pharmaceutical compositions suitable for use in the invention include compositions wherein the active ingredients are contained in an effective amount to achieve the intended purpose. The determination of an effective dose is well within the capability of those skilled in the art. For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example OAADPR or a related compound of the invention, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration. The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation. Normal dosage amounts may vary from about 0.1 ug to 100,000 ug, up to a total dose of about 1 gram, depending upon the route of administration. Guidance as to particular dosages and methods of delivery is provided in the literature and generally available to practitioners in the art.

The invention further provides diagnostic methods utilizing OAADPR, a related compound of the invention, and/or antibodies thereof. For example, antibodies which specifically bind OAADPR or a related compound of the invention may be used for the diagnosis of certain disease associated with alterations in sirtuin function and/or NAD flux such as neurodegenerative disorders, myopathies, cancer, and immune disorders characterized by alteration in sirtuin deacetylation and/or NAD metabolism, or in assays to monitor patients being treated with sirtuin (e.g., SIRT1) activators or agonists, or antagonists or inhibitors. Antibodies useful for diagnostic purposes may be prepared in the same manner as described above. Diagnostic assays for OAADPR or a related compound of the invention include methods which utilize the antibody and a label to detect OAADPR or a related compound of the invention in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used. A variety of protocols for measuring OAADPR or a related compound of the invention, including ELISAs, RIAs, and FACS, are known in the art and provide a basis for diagnosing altered or abnormal levels of OAADPR, or a related compound of the invention, in body tissues or fluids, or samples thereof. Normal or standard values for levels of OAADPR, or a related compound of the invention, are established by combining body fluids or cell extracts taken from normal mammalian subjects, preferably human, with antibody to the compound of interest under conditions suitable for complex formation. The amount of standard complex formation may be quantitated by various methods, preferably by photometric means. Levels of OAADPR or a related compound of the invention expressed in subject, samples from biopsied tissues are compared with the standard values. Deviation between standard and subject values establishes the parameters for diagnosing disease.

3. Kits

Also provided herein are kits, e.g., kits for therapeutic purposes or kits for modulating the lifespan of cells or modulating apoptosis. A kit may comprise one or more sirtuin-modulating compounds, e.g., in premeasured doses. A kit may optionally comprise devices for contacting cells with the compounds and instructions for use. Devices include syringes, stents and other devices for introducing a sirtuin-modulating compound into a subject (e.g., the blood vessel of a subject) or applying it to the skin of a subject.

In yet another embodiment, the invention provides a composition of matter comprising a sirtuin modulator of this invention and another therapeutic agent (the same ones used in combination therapies and combination compositions) in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The agent and the sirtuin modulator are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a sirtuin modulator of this invention; and b) another therapeutic agent such as those described elsewhere in the specification.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2$^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXEMPLIFICATION

The invention now being generally described, it will be more readily understood by reference to the following examples which are included merely for purposes of illustration of certain aspects and embodiments of the present invention, and are not intended to limit the invention in any way.

All reagents were obtained from commercial sources and used without further purification. NAD (inner salt form) was obtained from Sigma.

Example 1

Figure 1:
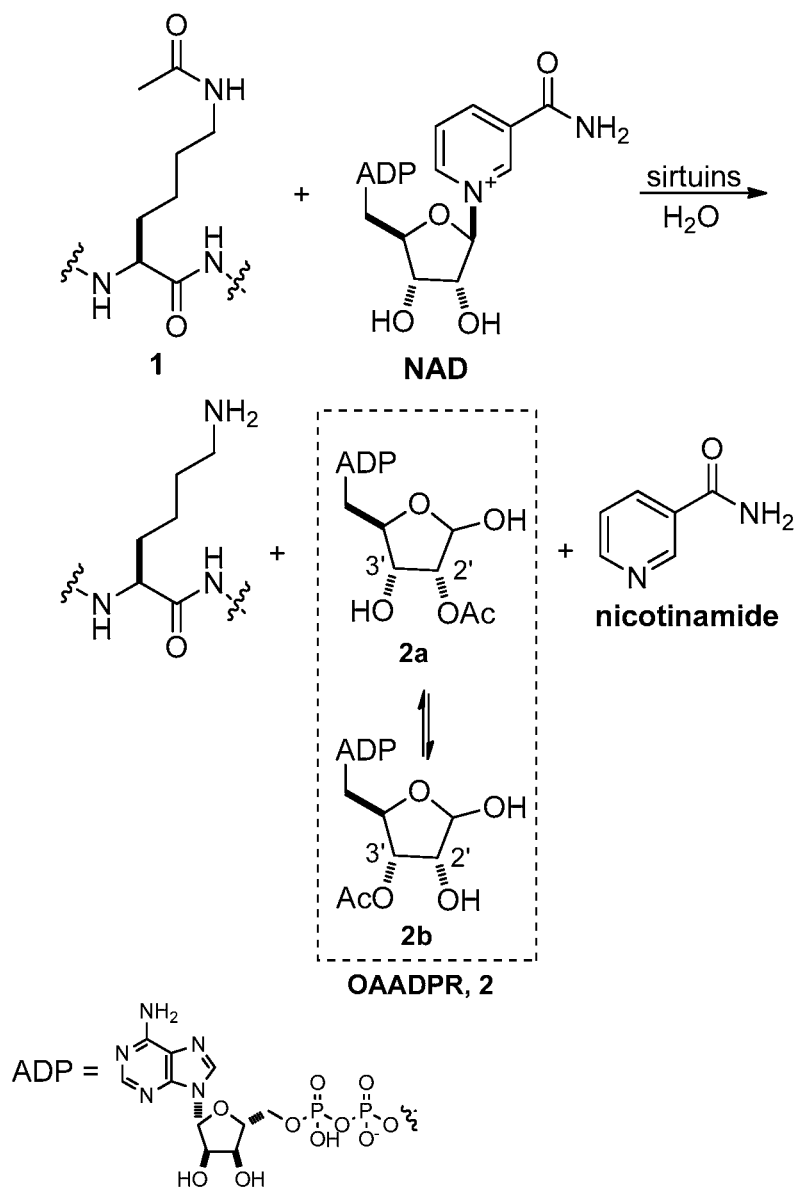
FIG. 1 shows sirtuin-mediated deacylation of an $N_\epsilon$-acetyllysine residue, which produces OAADPR and nicotinamide. Sirtuins remove the acetate from an $N_\epsilon$-acetyllysine residue by transferring the acetate to a molecule of NAD, with the concomitant displacement of nicotinamide and addition of a water molecule to generate 2'-O-acetyl-adenosine diphosphate-ribose (2a), which rapidly equilibrates to generate a 3'-O-acetyl-adenosine diphosphate-ribose (2b) isomer, the product comprising this mixture of esters (OAADPR, 2).

As shown in FIG. 1, sirtuins remove the acetate from an $N_\epsilon$-acetyllysine residue by transferring the acetate to a molecule of NAD, with the displacement of nicotinamide and addition of a water molecule to generate 2'-OAADPR which rapidly equilibrates to a mixture of 2' and 3'-O-OAADPR.

Example 2

Figure 2:
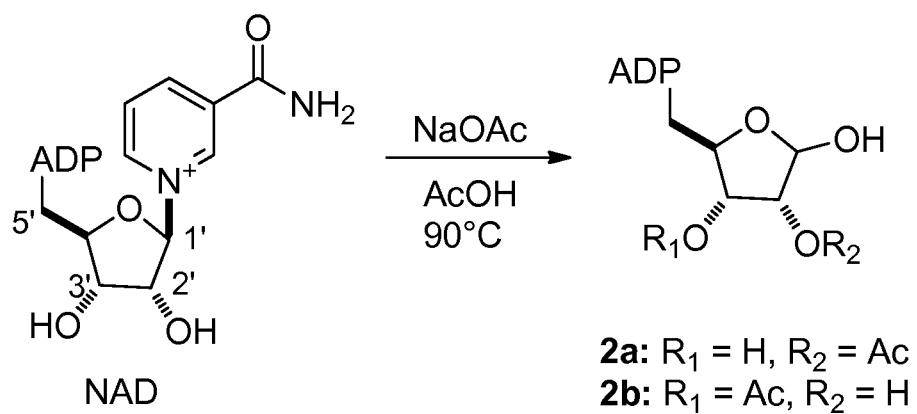
FIG. 2 shows preparation of 2'- and 3'-OAADPR from NAD and sodium acetate.

The new chemical preparation strategy is shown in FIG. 2. NAD and an excess amount of sodium acetate were stirred with glacial acetic acid as the solvent. Upon heating, the solids were dissolved to give a clear solution. Typically, the reaction was stopped after 90-95% consumption of NAD in order to avoid side reactions that lowered the product yield on further heating. The reaction was diluted with ethanol to give a precipitate consisting mainly of 2'- and 3'-OAADPR. Mass recoveries were high, and $^1$H NMR analysis showed the presence of only minor impurities. The remaining NAD can be removed by chromatography. Amine-linked silica gel resins were superior to polystyrene based amine resins for this separation. The mixture of 2'- and 3'-OAADPR isomers obtained from the reaction was identical to that described by Schramm (Sauve et al. (2001) *Biochemistry* 40: 15456).

Results

The reaction also succeeded with other short chain carboxylic acids. Linear and branched acids from $C_2$ through $C_7$ gave the corresponding 2'- and 3'-ADP-ribose esters (Table 1, FIG. 10). We found that separation of $C_3$ or longer chain alkanoic and alkenoic esters Cmpds. 4-11 from NAD could be accomplished via reversed-phase HPLC, with no ion chromatography necessary. Additionally, the 2'- and 3'-isomers of several longer chain, and alpha-branched, carboxylic acids were readily separable under the same conditions. In addition, the reaction was successful with benzoic acid, providing both 2' and 3'-O-benzoyl-ADP-ribose (Table 1, FIG. 10, Cmpd. 12). When NAD was heated with sodium octanoate in octanoic acid, no reaction was observed, likely due to the poor solubility of NAD in the reaction medium. (Table 1, FIG. 10, Entry 12) Heating NAD with trifluoroacetic acid (TFA) resulted in decomposition, and no TFA esters were observed. (Table 1, FIG. 10, Entry 13)

Similar to short chain monocarboxylates, it was discovered that dicarboxylates, tricarboxylates, and oxygenated carboxylic acids gave acyl-ADP-ribose products Cmpds. 13-17. (Table 1, FIG. 10) With these acids, pyridinium salts gave higher product yields than the sodium salts. The difference in yield was due to the lower reaction temperatures that could be employed with pyridinium salts, and the greater solubility of dicarboxylate and tricarboxylate pyridinium salts in ethanol, which facilitated product isolation. α-Oxygenated products proved difficult to isolate, though the products were clearly visible by HPLC/MS and $^1$H NMR. Following chromatography, α-oxygenated esters were always mixed with large amounts of ADP-ribose. Ester hydrolysis occurred if water was used in the reaction as a co-solvent.

When excess carboxylic acid was present, C-1' substitution occurred much faster than pyrophosphate displacement or pyrophosphate hydrolysis. Under these conditions, there is an intrinsic preference for NAD to undergo nucleophilic substitution at C-1', resulting in nicotinamide displacement. However, we did not observe any significant accumulation of C-1' acetate, even at lower reaction temperatures. As proposed by Schramm, the C-1' ester undergoes rapid equilibration to the more thermodynamically stable C-2' and C-3' isomers (Sauve et al. (2001) *Biochemistry* 40: 15456). Schuber and Cordes both showed that solvolysis of NAD occurs at C-1' and bears significant $S_N1$ character (Tarnus et al. (1988) *Bioorg. Chem.* 16: 38; Bull et al. (1978) *J. Biol. Chem.* 253: 5186). A similar mechanism would explain the preference for nucleophilic substitution of nicotinamide over pyrophosphate. The product mixture isolated from the reaction with sodium acetate was identical to that obtained from sirtuin-catalyzed protein deacetylation following equilibration of the 2' and 3' isomers. A small amount of the β-1' ester was present in the equilibrium mixtures as well (Sauve et al. (2001) *Biochemistry* 40: 15456; Cervantes-Laurean et al. (1997) *Meth. Enzymol.* 280: 275). $N_\epsilon$-propionyllysine and $N_\epsilon$-butyryllysine containing peptides have also been reported to undergo sirtuin catalyzed deacylation (Garrity et al. (2007) *J. Biol. Chem.* 282: 30239; Liu et al. *J. Biol. Chem.* 284: 32288; Smith and Denu (2007) *J. Biol. Chem.* 282: 37256). These peptides yield 2'/3'-O-propionyl- and 273'-O-butyryl-ADP-ribose, which were synthesized from the corresponding carboxylates. (Table 1, FIG. 10, Cmpds. 3 and 4) It is possible that lysine residues, $N_\epsilon$-acylated with an array of carboxylic acids, could potentially serve as substrates for sirtuins. Many other carboxylates commonly present in living cells will react with NAD and yield acyl-ADP-ribose esters. Acetyl-ADP-ribose (Table 1, FIG. 10, Cmpd. 2) is the only 2'/3'-ADP-ribose ester that has been identified in organisms. Since the reaction is broadly applicable to carboxylates and NAD, it is reasonable to speculate that anionic amino acid residues (e.g. glutamate or aspartate) would react with NAD to give ADP-ribose esters. Therefore, aspartate and glutamate residues may represent points of attachment for protein ADP-ribosylation (Hassa et al. (2006) *Microbio. Mol. Biol. Rev.* 70: 789).

Example 3

Ion Chromatography

Ion chromatography was performed using an ÄKTA prime automated LC system (Amersham Biosciences). Single step 4.7 g amine columns (Thomson Instrument Company) were used for chromatography. Columns were prewashed several times with elution buffer before use. Chromatograms were monitored by absorbance at 254 nM. Ion chromatography elution buffer compositions were as follows: solution A=57.25 mL glacial acetic acid diluted to 1000 mL final volume with deionized water (1M acetic acid), solution B=114.5 mL glacial acetic acid and 40 g $NaOH_{(s)}$ diluted to 1000 mL final volume with deionized water (1M sodium acetate, 1M acetic acid). The column was equilibrated with 90:10 A: B at a rate of 5 mL/min for 15 min. Up to 250 mg of crude product mixtures were loaded onto the column in 0.5-1 mL of water. Separation gradients were as follows: Gradient 1) 90:10 A: B for 5 min, 90:10 A:B to 50:50 A: B over 5 min, hold at 50% for 5 min, 50:50 A: B to 100% B over 5 min, then 100% B for 5 min; Gradient 2) 90:10 A: B for 5 min, 90:10 A:B to 100% B over 10 min, then 100% B for 5 min. At the end of a run, the column was again equilibrated with 90:10 A:B, and the next sample could be injected without regeneration. For long-term storage, columns were washed with 50 mL of water, then 50 mL of methanol, capped, and stored in methanol at ambient temperature.

Example 4

Desalting and Product Isolation

Product containing fractions were pooled and concentrated in vacuo with a rotary evaporator at or below 25° C. to 1-5 mL final volume. Alternatively, they were frozen and lyophilized until dry, then dissolved in a minimum amount of water. For the first desalting cycle, the aqueous solutions were diluted slowly with denatured alcohol (90:5:5 [v/v/v] ethanol: methanol: isopropanol), to a final concentration of 95:5 (v/v) alcohol: water. The product separated from this mixture as a white solid. The suspension was centrifuged at 3000 g at ambient temperature for 20 min, or until the precipitate settled to the bottom of the tube, and the supernatant decanted. The pellet contained the product, along with some sodium acetate. A second desalting cycle was performed as follows: 1) the pellet was dissolved in 1-2 mL of water and diluted slowly with denatured alcohol to a final concentration of 95:5 (v/v) alcohol: water 2) the suspension was centrifuged as before and 3) the supernatant was decanted and the pellet contained the product. The second desalting cycle was repeated for a total of three desalting cycles. Three cycles were sufficient to bring residual sodium acetate down to trace levels.

After desalting was complete, the pellet was dissolved in 2 mL of water, then concentrated in vacuo at 20° C. This was repeated to remove any residual alcohol. Finally, the residue was dissolved in water, frozen, and lyophilized to give the desired product as a solid.

Example 5

HPLC Purification

Reversed-phase HPLC purification was run using a Shimadzu Preparative Liquid Chromatography System equipped with a 30×100 mm XBridge C-18 column. Crude compounds were prepared as solutions in 0.5-3 mL of water for injection. Elution solvents were as follows: solution A—0.1% (v/v) trifluoroacetic acid in water, solution B-acetonitrile. Samples were eluted using a gradient of A: B, specified for each compound. Typically, NAD eluted just after the column void volume, followed by the 3'ADP-ribose ester, then the 2'ADP-ribose ester. With some compounds, a peak corresponding to the 1'ADP-ribose ester was observed between the 3' and 2' peaks. Product containing fractions were pooled, frozen, and lyophilized to dryness.

Example 6

Synthesis of 2'- and 3'-O-Acetyl-ADP-ribose (Table 1, FIG. 10, Cmpd. 2)

To 80 mg (0.75 mmol) of sodium carbonate was added 2 mL of glacial acetic acid. The mixture was stirred at ambient temperature until the sodium carbonate dissolved, then 250 mg (0.377 mmol) of NAD was added. The reaction was heated at 90° C. for 20 min, during which time the NAD completely dissolved. Heating removed, 5 mL of denatured alcohol (90:5:5 [v/v/v] ethanol: methanol: isopropanol) was slowly added to dilute the residual sodium acetate before precipitation of the product. The suspension was diluted more rapidly with another 13 mL of reagent alcohol and the precipitate was filtered to give a light tan solid. The crude product was purified via ion chromatography (Gradient 1) to give 88 mg (36%) of 2'- and 3'-OAADPR as the disodium salt. The product eluted at 50% B. MS (ESI+) m/z=602 (M+H)+.

If ion chromatography was not performed, a mixture of OAADPR and 5-10% NAD was obtained. The remaining sodium acetate was removed by subjecting the product to a second desalting cycle according to the procedure for Desalting and Product Isolation described above, to yield the product in 62%.

Example 7

Synthesis of 2'- and 3'-O-Propionyl-ADP-ribose (Table 1, FIG. 10, Cmpd. 3)

Prepared according to the same procedure described above for Cmpd 2. 32 mg (0.30 mmol) of $Na_2CO_3$, 0.8 mL propionic acid, and 100 mg (0.151 mmol) of NAD were used. The crude product was purified via HPLC (95% A, 5% B for 1 min; 5% to 25% B over 12.5 min, 25% to 85% B over 2.5 min) to give 11.4 mg (12%) 2'- and 3'-O-propionyl-ADP-ribose as a white solid. $T_R$=2.20-2.72 min (two overlapping peaks). MS (ESI+) m/z=616 (M+H)+.

Example 8

Synthesis of 2'- and 3'-O-n-Butyryl-ADP-ribose (Table 1, FIG. 10, Cmpd. 4)

Prepared from 32 mg (0.30 mmol) of $Na_2CO_3$, 0.8 mL of butyric acid, and 100 mg of NAD according to the same procedure as for Cmpd. 2. The crude product was purified via HPLC (95% A, 5% B for 1 min; 5% to 20% B over 12 min; 20% B for 0.5 min; 20% to 85% B over 2.5 min) to give 4.6 mg (4.8%) of 3'-O-butyryl-ADP-ribose ($T_R$=3.61 min) and 1.9 mg (2.1%) of 2'-O-butyryl-ADP-ribose ($T_R$=4.75 min), both as white solids. MS (ESI+) m/z=630 (M+H)+.

Example 9

Synthesis of 2'- and 3'-O-isobutyryl-ADP-ribose (Table 1, FIG. 10, Cmpd. 5)

Prepared from 80 mg (0.75 mmol) of $Na_2CO_3$, 2 mL of isobutyric acid and 250 mg of NAD according to the same procedure described above for Cmpd. 2. The crude product was purified via HPLC (100% A, 0% B to 92% A, 8% B over 1.5 min; 8% to 20% B over 4.75 min; 20% to 95% B over 2 min; step to 95% A, 5% B, hold for 1.75 min) to give 4.7 mg (2.0%) of 3'-O-isobutyryl-ADP-ribose ($T_R$=3.27 min) and 6.3 mg (2.7%) of 2'-O-isobutyryl-ADP-ribose ($T_R$=3.61 min), both as white solids. MS (ESI+) m/z=630 (M+H)+.

Example 10

Synthesis of 2'- and 3'-O-trimethylacetyl-ADP-ribose (Table 1, FIG. 10, Cmpd. 6)

To 80 mg (0.75 mmol) of sodium carbonate and 2.1 g (21 mmol) of trimethylacetic acid was added 8 mL of N,N-dimethylacetamide (DMA). The mixture was stirred until all of the sodium carbonate had dissolved, then 250 mg (0.376 mmol) of NAD was added. The reaction was heated at 95° C. for 50 min, 100 mL of ethanol was added to give a precipitate. The precipitate was filtered and washed with additional ethanol. The precipitate was purified via HPLC (100% A, 0% B to 92% A, 8% B over 1.5 min; 8% to 20% B over 4.75 min; 20% to 95% B over 2 min; step to 95% A, 5% B, hold for 1.75 min) to give 1.7 mg (0.7%) of 3'-O-tert-butyryl-ADP-ribose ($T_R$=4.17 min), and 1.7 mg (0.7%) of 2'-O-tert-butyryl-ADP-ribose ($T_R$=4.77 min), both as white solids. MS (ESI+) m/z=644 (M+H)+.

Example 11

Synthesis of 2'- and 3'-O-trans-2-Butenoyl-ADP-ribose (Table 1, FIG. 10, Cmpd. 7)

To 32 mg (0.30 mmol) of sodium carbonate and 700 mg (8.13 mmol) of crotonic acid was added 5 mL of DMA. The mixture was stirred until all of the sodium carbonate had dissolved, then 100 mg (0.15 mmol) of NAD was added. The reaction was heated at 95° C. for 15 min and 100 mL of ethanol was added to give a precipitate. The precipitate was filtered and washed with additional ethanol. The residue was purified via HPLC (95% A, 5% B to 75% A, 25% B over 15 min; 25% to 95% B over 5 min) to give 6.9 mg (7.3%) of 3'-O-(2-butenoyl)-ADP-ribose ($T_R$=3.16 min), and 9.1 mg (9.6%) of 2'-O-(2-butenoyl)-ADP-ribose ($T_R$=3.81 min), both as white solids. MS (ESI+) m/z=628 (M+H)+.

Example 12

Synthesis of 2'- and 3'-n-Pentanoyl-ADP-ribose (Table 1, FIG. 10, Cmpd. 8)

Prepared from 80 mg (0.75 mmol) of $Na_2CO_3$, 2 mL of valeric acid, and 250 mg (0.376 mmol) of NAD, according to the same procedure described above for Cmpd. 2. The crude product was purified via HPLC (95% A, 5% B for 1 min; 5% to 75% B over 12 min; 75% to 95% B over 2 min) to give 5.1 mg (2.1%) of 3'-O-n-pentanoyl-ADP-ribose ($T_R$=4.69 min), and 39.1 mg (16.1%) of 2'-O-n-pentanoyl-ADP-ribose ($T_R$=5.32 min), both as white solids. MS (ESI+) m/z=644 (M+H)+.

Example 13

Synthesis of 2'- and 3'-O-(3-methyl-but-2-enoyl)-ADP-ribose (Table 1, FIG. 10, Cmpd. 9)

Prepared from 32 mg (0.30 mmol) of sodium carbonate, 700 mg (7.0 mmol) of 3,3-dimethylacrylic acid, 5 mL of DMA, and 100 mg (0.15 mmol) of NAD, according to the same procedure described above for 7. The crude product was purified via HPLC (95% A, 5% B to 75% A, 25% B over 15 min; 25% to 95% B over 5 min) to give 3.9 mg (4.0%) of 3'-O-(3-methyl-but-2-enoyl)-ADP-ribose ($T_R$=4.25 min), and 9.3 mg (9.6%) of 2'-O-(3-methyl-but-2-enoyl)-ADP-ribose ($T_R$=5.49 min), both as white solids. MS (ESI+) m/z=642 (M+H)+.

Example 14

Synthesis of 2'- and 3'-O-n-hexanoylADPribose (Table 1, FIG. 10, Cmpd. 10)

To a solution of 80 mg (0.75 mmol) of sodium carbonate, dissolved in 2 mL (16 mmol) of n-hexanoic acid at 95° C. was added 250 mg (0.376 mmol) of NAD. The reaction was stirred at 95° C. for 10 min and then cooled. The mixture was diluted with 1-2 mL of water, then purified by HPLC (90% A, 10% B for 1 min, 10% B to 95% B over 14 min) to give 20.9 mg (8.4%) of 3'-O-n-hexanoyl-ADP-ribose ($T_R$=5.01 min) and 20.3 mg (8.2%) of 2'-O-n-hexanoyl-ADP-ribose ($T_R$=5.67 min), both as white solids. MS (ESI$^+$) m/z=658 (M+H)$^+$.

Example 15

Synthesis of 2'- and 3'-O-n-heptanoyl-ADP-ribose (Table 1, FIG. 10, Cmpd. 11)

Prepared from 80 mg (0.75 mmol) of $Na_2CO_3$, 2 mL (14 mmol) of n-heptanoic acid, and 250 mg (0.376 mmol) of NAD, according to the same procedure described for Cmpd. 10. The crude product was purified by HPLC (90% A, 10% B for 1 min, 10% B to 95% B over 14 min) to give 2.4 mg (0.9%) of 3'-O-n-heptanoyl-ADP-ribose ($T_R$=6.09 min, overlap with 1'-isomer at 6.24 min) and 0.6 mg (0.2%) of 2'-O-n-heptanoyl-ADP-ribose ($T_R$=6.64 min), both as white solids. MS (ESI$^+$) m/z=672 (M+H)$^+$.

Example 16

Synthesis of 1'-, 2'- and 3'-O-benzoyl-ADP-ribose (Table 1, FIG. 10, Cmpd. 12)

To 32 mg (0.30 mmol) of sodium carbonate and 700 mg of benzoic acid was added 5 mL of DMA. The mixture was stirred at 50° C. until all the sodium carbonate had dissolved. 100 mg (0.15 mmol) of NAD was added along with 2 mL of water. The reaction was stirred at 95° C. for 20 min. 100 mL of ethanol was added to give a precipitate. The precipitate was filtered and washed with additional ethanol. The residue was purified via HPLC (95% A, 5% B for 1 min; 5% to 25% B over 12.5 min, 25% to 85% B over 2.5 min) to give 6.5 mg (6.5%) of 3'-O-benzoyl-ADP-ribose ($T_R$=5.47 min), 0.7 mg (0.7%) of 1'β-O-benzoylADPribose ($T_R$=6.02 min), and 1.7 mg (1.7%) of 2'-O-benzoyl-ADP-ribose ($T_R$=7.19 min), as white solids. MS (ESI$^+$) m/z=664 (M+H)$^+$.

Example 17

Synthesis of 2'- and 3'-O-succinyl-ADP-ribose (Table 1, FIG. 10, Cmpd. 13)

A mixture of 500 mg (4.23 mmol) of succinic acid, and 500 μL (6.18 mmol) of pyridine was heated and stirred at 90° C. until the mixture was homogeneous. To the mixture was added 100 mg (0.15 mmol) of NAD, and the reaction was stirred at 90° C. for 20 min. The heat was removed and 10 mL of denatured alcohol was added. The resulting suspension was filtered to give a sticky solid. This was purified via ion chromatography (Gradient 1) to give 20 mg (18%) of 2'- and 3'-O-succinoyl-ADP-ribose trisodium salt as a white powder. The product eluted at 50% B. MS (ESI$^+$) m/z=660 (M+H)$^+$.

Example 18

Synthesis of 2'- and 3'-O-citryl-ADP-ribose (Table 1, FIG. 10, Cmpd. 14)

Prepared from 400 mg (1.90 mmol) of citric acid monohydrate, 400 μL (4.95 mmol) of pyridine, and 100 mg (0.15 mmol) of NAD, according to the same procedure described above for Cmpd. 13. The crude product was purified by ion chromatography (Gradient 2) to give 29 mg (24%) of 2'- and 3'-O-citryl-ADP-ribose tetrasodium salt as a beige solid. The product eluted at 100% B. MS (ESI$^+$) m/z=734 (M+H)$^+$.

Example 19

Synthesis of 2'- and 3'-O-malyl-ADP-ribose (Table 1, FIG. 10, Cmpd. 15)

A mixture of 400 mg (2.98 mmol) of malic acid and 400 μL (4.95 mmol) of pyridine was heated and stirred at 90° C. until the mixture was homogeneous. To the mixture was added 100 mg (0.15 mmol) of NAD, and the reaction was stirred at 90° C. for 20 min. The heat was removed and 10 mL of denatured alcohol was added. The resulting suspension was centrifuged (3000 g, 20° C., 20 min). The supernatant was decanted, the pellet was dissolved in 500 μL of water and diluted with 10 mL of denatured alcohol. This suspension was centrifuged again (300 g, 20° C., 20 min) and the supernatant was decanted to give the crude product as a solid. This was purified via ion chromatography (Gradient 1) to give 13.9 mg (12%) of 2'- and 3'-O-malyl-ADP-ribose trisodium salt as a white solid. The product eluted from the column at 50% B, immediately after ADP-ribose. MS (ESI$^+$) m/z=676 (M+H)$^+$.

Example 20

NMR

NMR Spectra were recorded with a Bruker Avance III 300 MHz spectrometer. All $^1$H NMR spectra were run in $D_2O$ using HOD (4.79 ppm) as an internal reference. Chemical shift data are reported in parts per million. Spectral multiplicity abbreviations are: s-singlet, d-doublet, t-triplet, dd-doublet of doublets, m-multiplet. Integration refers to the number of protons per signal. In cases where a signal can be assigned to one anomer, the integration value may be a fraction of a proton. Coupling constants are reported in Hertz. $^1$H NMR resonances were assigned using COSY experiments (COSY spectra not shown.) All OH and $NH_2$ protons were in rapid exchange with the solvent and were not visible in any recorded spectra.

Example 21

Strong Cation Exchange (SCX) Flash Chromatography for OAADPR

A benzenesulfonic acid linked silica gel column (SCX silica gel) was eluted with 1M sodium acetate and 0.01 M acetic acid in water to obtain the sodium form (Na$^+$form). To condition a newer column, the column was washed with 1M sodium acetate and 0.01 M acetic acid in water every three days for at least 15 days to condition the column. After conditioning was complete, the column was washed with methanol, and then stored in methanol.

To 80 mg of $Na_2CO_3$ was added 2 mL of glacial acetic acid. The mixture was stirred at 85° C. until all the $Na_2CO_3$ reacted. 250 mg of NAD was added and the mixture was stirred at 85° C. for 15 min, cooled to below 75° C. and diluted with 20 mL of $CH_3CN$. The precipitate was filtered, suspended in 5 mL of $CH_3CN$, and filtered again to give crude OAADPR.

A 4.7 g SCX silica gel column (Na$^+$form) was equilibrated with $CH_3CN$. 10 mg of crude OAADPR was dissolved in 0.1 mL of water and injected onto the column. The column was eluted at 5 mL/min with the following solvents:
1. $CH_3CN$ (20 mL)
2. 10% $H_2O$: 90% $CH_3CN$ (20 mL)
3. 20% $H_2O$: 80% $CH_3CN$ and
4. 20-30% ramp $H_2O$ in $CH_3CN$ over 5 min.

The product began to elute at 20% H₂O, and finished eluting during the 20-30% gradient. OAADPR containing fractions were concentrated in vacuo, taken up in water, frozen, and lyophilized to give OAADPR as a white solid. The column was regenerated by eluting with 1M sodium acetate and 0.01M acetic acid in water, then with methanol, and stored in methanol.

Example 22

Synthesis of deuterated
O-acetyl-adenosine-diphosphate-ribose
(D₃-OAADPR)

A 4.7 gram SCX column (Strong Cation Exchange column) was washed with 100 mL of 1 M NaOAc (aq). The column was washed with a minimum of 200 mL of Methanol until all of the NaOAc was removed. The eluent was checked by NMR for the presence of NaOAc. Once the NaOAc had been successfully removed, the column was equilibrated with ACN.

32 mg of Na₂CO₃ was dissolved in 0.8 mL of Acetic acid-D4. The mixture was heated to 85° C. and 100 mg of NAD was added. The reaction mixture was stirred for 30 minutes then checked by LC/MS, which still showed the presence of NAD. The reaction mixture was heated for an additional 20 minutes and another LC/MS sample was checked. Some NAD was still present, so the reaction was heated for an additional 10 minutes. The reaction mixture was allowed to cool and 10 mL of Ethanol was added to precipitate out the solids. The suspension was transferred to a centrifuge tube (an additional 5 mL of Ethanol was used to complete the transfer) and the suspension was centrifuged at 5000 rpm for 5 minutes. The supernatant was decanted off and the solid was dissolved in a minimum amount of water and injected onto the SCX column. The column was eluted with 20 mL of Acetonitrile, then 100 mL of a gradient going from ACN to MeOH, then with 100 mL MeOH. The product began eluting at a higher percentage of MeOH. The column was then flushed with 1 M NaOAc (aq). Product containing fractions were concentrated down on a rotavap. The residue was dissolved in water and rotavaped again to remove residual solvents. The residue was again dissolved and lyophilized. 28 mg (31% yield) of methyl deuterated OAADPR was obtained as a white powder.

EQUIVALENTS

The present invention provides among other things sirtuin-activating compounds and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

We claim:

1. A method of non-enzymatic synthesis of compound (III), a 2'-O— or 3'-O-carboxylic ester of the ribose moiety of adenosine-5'-diphosphate ribose (ADP-ribose) or a 2'-O— or 3'-O-carboxylic ester of the ribose moiety of a non-adenosine nucleoside-5'-diphosphate ribose (NDP-ribose) analog, comprising reacting compound (I) defined as
   (i) nicotinamide adenine dinucleotide (NAD) or a non-adenosine nucleoside-5'-diphosphate ribose (NDP-ribose) analog (I) wherein the non-adenosine substituent moiety is selected from the group consisting of 5'-guanosinyl, 5'-(5-methyluridinyl), 5'-uridinyl, and 5'-cytidinyl; and
   (ii) the variable LG (leaving group) is selected from the group consisting of a 1-nicotinamidinyl moiety, a 1-nicotinic acid-derived moiety and a halide ion;
with a carboxylate ion (II) to produce a mixture of the two O-acylated compounds (III a) and (III b)

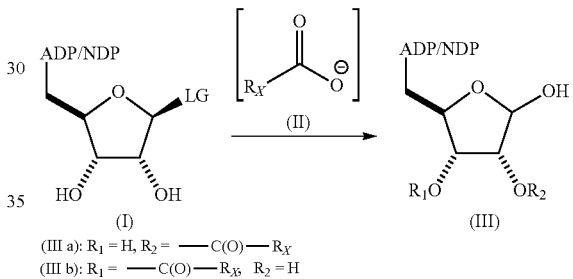

(III a): R₁ = H, R₂ = —C(O)—Rₓ
(III b): R₁ = —C(O)—Rₓ, R₂ = H wherein one of R₁ and R₂ is H, and the other is —C(O)—Rₓ such that the product (III) comprises a mixture of 2'-O-carboxyl-ADP/NDP-ribose (III a, wherein R₁ is H and R₂ is —C(O)—Rₓ) and 3'-O-carboxyl-ADP/NDP-ribose (III b, wherein R₁ is —C(O)—Rₓ and R₂ is H), wherein Rₓ is an optionally substituted C₁-C₁₂ straight or branched alkyl or alkenyl moiety, or an optionally substituted carbocyclyl moiety that is saturated, unsaturated, or aromatic 5-7 membered monocyclic ring or 8-12 membered bicyclic ring, or an
optionally substituted heterocyclyl moiety that is a saturated, unsaturated, or aromatic 5-7 membered monocyclic ring or 8-12 membered bicyclic rings comprising one or more heteroatoms selected from N,O, and S.

2. The method of claim 1, wherein (I) is NAD.

3. The method of claim 2, wherein the carboxylate (II) is acetate and the product is a mixture of 2'-O-acetyl ADP-ribose (III a) and 3'-O-acetyl ADP-ribose (III b).

4. The method of claim 1, wherein the carboxylate (II) is selected from the group consisting of propionate, n-butyrate, isobutyrate, trimethylacetate, trans-2-butenoate, n-pentanoate, 3,3-dimethylacrylate, n-hexanoate, n-heptanoate, benzoate, succinate, citrate, DL-lactate and L-malate.

5. The method of claim 1, wherein the leaving group is a halide ion selected from the group consisting of Cl⁻, Br⁻, I⁻ and F⁻.

6. The method of claim 1, wherein the carboxylate is reacted with the nicotinamide adenine dinucleotide (NAD) or analog thereof at a temperature of 20° C. to 120° C. in a reaction mixture optionally further comprising an organic solvent.

7. The method of claim 6, further comprising wherein the carboxylate is formed by the reaction of an inorganic or an organic base with a carboxylic acid before the addition of the NAD or analog thereof.

8. The method of claim 7, wherein the inorganic base is $Na_2CO_3$ or $NaHCO_3$.

9. The method of claim 7, wherein the organic base is selected from the group consisting of a trialkylamine, a 5 to 6-membered nitrogen containing heterocycle, and an optionally $C_1$-$C_4$ substituted 5 to 6-membered nitrogen containing heterocycle.

10. The method of claim 7, wherein the carboxylic acid is selected from the group consisting of propionic acid, n-butyric acid, isobutyric acid, trimethylacetic acid, trans-butenoic acid, n-pentanoic acid, 3, 3-dimethylacrylic acid, n-hexanoic acid, n-heptanoic acid, benzoic acid, succinic acid, citric acid, DL-lactic acid, and L-malic acid.

11. The method of claim 7, wherein the carboxylic acid is acetic acid.

12. The method of claim 6, wherein the organic solvent is selected from the group consisting of dimethylformamide, N,N-dimethylacetamide, N-methyl-2-pyrrolidinone, trimethyl phosphate, triethyl phosphate, formamide and dimethylsulfone.

13. The method of claim 6, wherein the temperature is about 85° C. to 95° C.

14. The method of claim 7, wherein the inorganic base is $Na_2CO_3$, the nicotinamide adenine dinucleotide (NAD) or analog thereof is NAD, and the carboxylic acid is acetic acid.

15. The method of claim 7, wherein the organic base is pyridine, the nicotinamide adenine dinucleotide (NAD) or analog thereof is NAD and the carboxylic acid is selected from the group consisting of succinic acid, citric acid, DL-lactic acid and L-malic acid.

16. The method of claim 1, further comprising the step of purifying the product by ion chromatography.

17. The method of claim 6, further comprising the step of purifying the product by ion chromatography.

18. The method of claim 16, further comprising wherein ion chromatography is performed on an aminopropyl functionalized silica gel column.

19. The method of claim 1, further comprising wherein when $R_x$ is optionally substituted, it is optionally substituted with one or more substituents selected from the group consisting of a halogen, an alkyl, an amine, a hydroxyl, an O-alkyl, a N-alkyl, an aryl, an arylalkyl, a cycloalkyl, a cycloheteroalkyl, a heteroalkyl, a heteroaryl, and a heteroarylalkyl.

20. A method for the non-enzymatic synthesis of a mixture of (III a) and (III b) that are 2'-O— and 3'-O-carboxylic acid esters of the ribose moiety of adenosine diphosphate ribose (ADP-ribose) comprising reacting compound (IV) defined as
nicotinamide adenine dinucleotide (NAD) wherein Y is a 1-nicotinamidyl moiety, or an analog thereof wherein Y is a 1-nicotinic acid acid-derived moiety;
with a carboxylate ion (II) to produce the O-acylated ADP-ribose products defined by formulas (III a) and (III b),

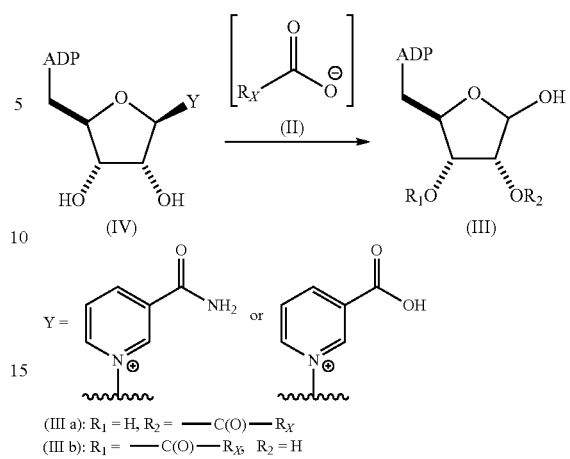

(III a): $R_1$ = H, $R_2$ = —C(O)—$R_X$
(III b): $R_1$ = —C(O)—$R_X$, $R_2$ = H wherein the product (III, wherein one of $R_1$ and $R_2$ is H, and the other is —C(O)—$R_x$) comprises a mixture of 2'-O-acyl-ADP-ribose (III a, wherein $R_1$ is H and $R_2$ is —C(O)—$R_x$) and 3'-O-acyl-ADP-ribose (III b, wherein $R_1$ is —C(O)—$R_x$ and $R_2$ is H), wherein $R_x$ is an optionally substituted $C_1$-$C_{12}$ straight or branched alkyl or alkenyl moiety, or an optionally substituted carbocyclyl moiety that is a saturated, unsaturated, or aromatic 5-7 membered monocyclic ring or 8-12 membered bicyclic ring, or an optionally substituted heterocyclyl moiety that is a saturated, unsaturated, or aromatic 5-7 membered monocyclic ring or 8-12 membered bicyclic rings comprising one or more heteroatoms selected from N, O, and S.

21. The method of claim 20, wherein Y is 1-nicotinamidyl.

22. The method of claim 20, wherein Y is a 1-nicotinic acid-derived moiety.

23. The method of claim 20, wherein the carboxylate is acetate and the product is O-acetyl-ADP ribose comprising a mixture of 2'-O-acetyl-ADP-ribose (III a) and 3'-O-acetyl-ADP-ribose (III b).

24. The method of claim 20, wherein the carboxylate is formed by the reaction of an inorganic base with a carboxylic acid before the addition of the NAD or analog thereof.

25. The method of claim 24, wherein the inorganic base is $Na_2CO_3$ or $NaHCO_3$.

26. The method of claim 20, wherein the carboxylate (III) is formed by the reaction with acetic acid.

27. The method of claim 20, wherein the nicotinamide adenine dinucleotide (NAD) or analog thereof is NAD.

28. The method of claim 20, wherein the reaction temperature is about 85° C. to 95° C.

29. The method of claim 20, wherein the carboxylate is formed by the reaction of a carboxylic acid and $Na_2CO_3$, the nicotinamide adenine dinucleotide (NAD) or analog thereof is NAD, and the carboxylic acid is acetic acid.

30. The method of claim 20, further comprising the step of purifying the product by ion chromatography.

31. The method of claim 20, further comprising wherein when $R_x$ is optionally substituted, it is optionally substituted with one or more substituents selected from the group consisting of a halogen, an alkyl, an amine, a hydroxyl, an O-alkyl, a N-alkyl, an aryl, an arylalkyl, a cycloalkyl, a cycloheteroalkyl, a heteroalkyl, a heteroaryl, and a heteroarylalkyl.

32. A method of non-enzymatic syntheses of mixtures of O-acetyl esters (VII a) and (VII b) of adenosine diphosphate ribose (ADP-ribose) comprising
reacting nicotinamide adenine dinucleotide (NAD) (V) with acetic acid (VI)
to produce O-acetyl-ADP-ribose product (VII),

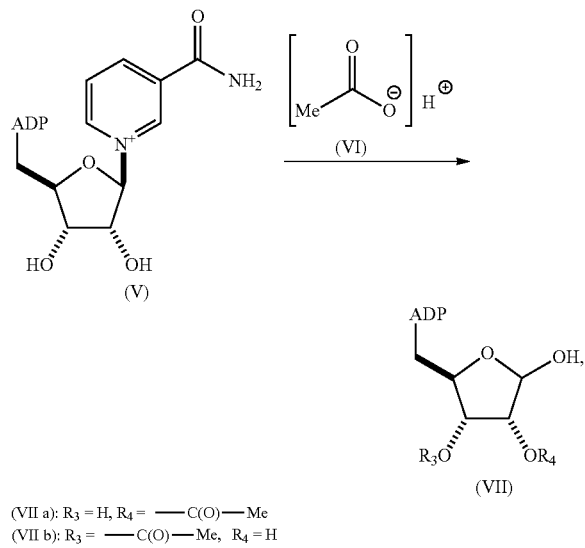

(VII a): $R_3 = H$, $R_4 = $ —C(O)—Me
(VII b): $R_3 = $ —C(O)—Me, $R_4 = H$ wherein the product (VII) comprises a mixture of 2'- and 3'-O-acetyl-ADP-ribose (VII a and VII b).

33. The method of claim 32, further comprising wherein the methyl groups of products (VII a and VII b) are deuterated.

34. The method of claim 32, further comprising the step of purifying the product by ion chromatography.

35. A mixture of 2'-O— and 3'-O-acyl esters of adenosine diphosphate ribose (ADP-ribose) compound or a non-adenosine nucleoside diphosphate ribose (NDP-ribose) analog thereof represented by Structural Formulas (VIII a) and (VIII b):

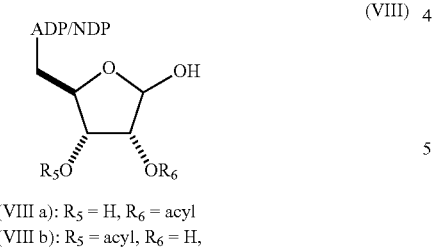

(VIII a): $R_5 = H$, $R_6 = $ acyl
(VIII b): $R_5 = $ acyl, $R_6 = H$, comprising a mixture of 2'-O-acyl-ADP-ribose (VIII a) and 3'-O-acyl-ADP-ribose (VIII b) or non-adenosine nucleoside diphosphate ribose (NDP-ribose) analogs thereof,
wherein the non-adenosine substituent moiety is selected from the group consisting of 5'-guanosinyl, 5'-(5-methyluridinyl), 5'-uridinyl, and 5'-cytidinyl;
wherein one of $R_5$ and $R_6$ is H, and the other is a an acyl moiety having the structure —C(O)—$R_x$, where $R_x$ is an optionally substituted $C_4$-$C_{12}$ straight, branched alkyl or alkenyl moiety, or an acyl moiety selected from the group consisting of —C(O)—($C_4$-$C_6$)alkyl, —C(O)—CH(OH)—($C_1$-$C_3$ alkyl), —C(O)—($C_1$-$C_3$)alkyl-COOR', —C(O)—($C_1$-$C_3$)alkyl-C(OR')(COOR')—($C_1$-$C_3$)alkyl —COOR'), —C(O)—CH(OR')—COOR', —C(O)—CR'—(CH$_3$)$_2$, —C(O)—CR'=CR—($C_1$-$C_3$ alkyl), and —C(O)—CR'=C(CH$_3$)$_2$, and each R' is independently selected from H and optionally substituted $C_1$-$C_3$ alkyl.

36. The compound of claim 35, wherein one of $R_5$ and $R_6$ is H, and the other is selected from the group consisting of —C(O)—CH—(CH$_3$)$_2$ (acyl moiety derived from isobutyrate), —C(O)—C(CH$_3$)$_3$ (acyl moiety derived from trimethylacetate), —C(O)—CH=CH—CH$_3$ (acyl moiety derived from trans-2-butenoate), —C(O)—CH$_2$—CH$_2$—CH$_2$—CH$_3$ (acyl moiety derived from n-pentanoate), —C(O)—CH=C(CH$_3$)$_2$ (acyl moiety derived from 3,3-dimethylacrylate), —C(O)—(CH$_2$)$_4$—CH$_3$ (acyl moiety derived from n-hexanoate), —C(O)—(CH$_2$)$_5$—CH$_3$ (acyl moiety derived from n-heptanoate), —C(O)—C$_6$H$_5$ (acyl moiety derived from benzoate), —C(O)—(CH$_2$)$_2$—C(O)—OH, (acyl moiety derived from succinate), —C(O)—CH$_2$—C(OH)(COOH)—CH$_2$—COOH (acyl moiety derived from citrate), —C(O)—CH(OH)—CH$_3$ (acyl moiety derived from DL-lactate) and —C(O)—CH(OH)—CH$_2$—COOH (acyl moiety derived from L-malate).

37. The compound of claim 35, wherein the mixture of compounds of Structural Formulas (VIII a) and (VIII b) are isolated with at least 90% molar purity.

38. The compound of claim 35, wherein the mixture of compounds of Structural Formulas (VIII a) and (VIII b) are isolated with at least 95% molar purity.

39. The compound of claim 35, wherein the mixture of compounds of Structural Formulas (VIII a) and (VIII b) are isolated with at least 99% molar purity.

40. The compound of claim 35, further comprising wherein when R' is an optionally substituted $C_1$-$C_3$ alkyl, it is optionally substituted with one or more substituents selected from the group consisting of a halogen, an alkyl, an amine, a hydroxyl, an O-alkyl, a N-alkyl, an aryl, an arylaklyl, a cycloalkyl, a cycloheteroalkyl, a heteroalkyl, a heteroaryl, and a heteroarylalkyl.

41. The compound of claim 35, further comprising wherein when the R' is an optionally substituted $C_1$-$C_3$ alkyl, it is optionally substituted with one or more substituents selected from the group consisting of a halogen, an alkyl, an amine, and a hydroxyl.

42. An isolated mixture of 2'-O— and 3'-O-propionyl esters of adenosine diphosphate ribose (ADP-ribose) compound or a non-adenosine nucleoside diphosphate ribose (NDP-ribose) analog thereof represented by Structural Formula (IX):

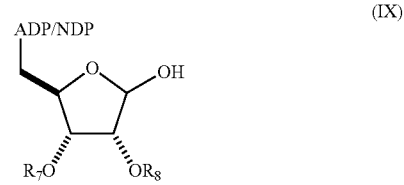

(IX a): $R_7 = H$, $R_8 = $ —C(O)—CH$_2$—CH$_3$
(IX b): $R_7 = $ —C(O)—CH$_2$—CH$_3$, $R_8 = H$ comprising a mixture of 2'-O-propionyl-ADP-ribose (IX a) and 3'-O-propionyl-ADP-ribose (IX b) or non-adenosine nucleoside diphosphate ribose (NDP-ribose) analog thereof, wherein the non-adenosine substituent moiety is selected from the group consisting of 5'-guanosinyl, 5'-(5-methyluridinyl), 5'-uridinyl, and 5'-cytidinyl;

wherein one of $R_7$ and $R_8$ is H, and the other is —C(O)—CH$_2$—CH$_3$, and the mixture of compound is isolated with at least 90% molar purity.

* * * * *